US005759837A

United States Patent [19]
Kuhajda et al.

[11] Patent Number: 5,759,837
[45] Date of Patent: Jun. 2, 1998

[54] CHEMOTHERAPY FOR CANCER BY INHIBITING THE FATTY ACID BIOSYNTHETIC PATHWAY

[75] Inventors: Francis P. Kuhajda, Lutherville; Gary R. Pasternack, Baltimore, both of Md.

[73] Assignee: John Hopkins University, Baltimore, Md.

[21] Appl. No.: 188,425

[22] Filed: Jan. 24, 1994

Related U.S. Application Data

[63] Continuation-in-part of Ser. No. 96,908, Jul. 26, 1993, abandoned, which is a continuation-in-part of Ser. No. 917,716, Jul. 24, 1992, abandoned, which is a continuation-in-part of Ser. No. 735,522, Jul. 26, 1991, abandoned, which is a continuation-in-part of Ser. No. 622,407, Dec. 4, 1990, abandoned, which is a continuation of Ser. No. 297,722, Jan. 17, 1989, abandoned.

[51] Int. Cl.$^6$ .............................. C12N 9/04; C12N 9/10
[52] U.S. Cl. .................... 435/193; 435/190; 424/248.52; 424/417
[58] Field of Search ...................... 514/12, 64; 424/94.1, 424/248.52, 417; 435/190, 193

[56] References Cited

U.S. PATENT DOCUMENTS

| | | | |
|---|---|---|---|
| 3,535,509 | 10/1970 | Hata et al. | 195/80 |
| 3,630,846 | 12/1971 | Hata et al. | 195/80 |
| 3,897,428 | 7/1975 | Omura et al. | 260/247.7 |
| 3,909,361 | 9/1975 | Hata et al. | 260/210 |
| 4,000,164 | 12/1976 | Parker | 260/347.4 |
| 4,011,334 | 3/1977 | Parker | 424/275 |
| 4,032,647 | 6/1977 | Parker | 424/295 |
| 4,110,351 | 8/1978 | Parker | 260/347.2 |
| 4,146,623 | 3/1979 | Parker | 424/248.52 |
| 4,328,246 | 5/1982 | Gold | 424/308 |
| 4,602,099 | 7/1986 | Parker | 549/749 |
| 4,738,984 | 4/1988 | Parker | 514/93 |
| 4,789,630 | 12/1988 | Block et al. | 435/5 |
| 4,883,665 | 11/1989 | Miyazima et al. | 424/417 |
| 4,946,774 | 8/1990 | Oh | 435/9.92 |
| 4,968,494 | 11/1990 | Claremon et al. | 424/94.64 |
| 5,004,811 | 4/1991 | Bommer et al. | 540/145 |
| 5,143,907 | 9/1992 | Spielvogel | 514/64 |
| 5,185,149 | 2/1993 | Baldwin et al. | 424/94.63 |
| 5,188,830 | 2/1993 | Atkinson et al. | 424/94.63 |
| 5,190,969 | 3/1993 | Blumenstein et al. | 514/422 |
| 5,539,132 | 7/1996 | Royer et al. | 549/545 |

FOREIGN PATENT DOCUMENTS

| | | |
|---|---|---|
| 0 246 734 | 11/1987 | European Pat. Off. . |
| 0 374 886 | 6/1990 | European Pat. Off. . |
| 252 616 | 12/1987 | Germany . |
| 59-255115 | 12/1984 | Japan . |
| 60-058917 | 4/1985 | Japan . |
| 1-132542 | 5/1989 | Japan . |
| 2-113850 | 4/1990 | Japan . |
| 2-247125 | 10/1990 | Japan . |
| WO 89/04963 | 6/1989 | WIPO . |

OTHER PUBLICATIONS

Bacchi, et al., "Effects of Some Antitumor Agents on Growth and Glycotytic Enzymes of the Flagellate *Crithidia*," Journal of Bacteriology. 98:23–28 (1969).

Furnica, et al., "Mecanismes Biochimiques Impliques Dans La Sensibitisation Des Organismes Vivants Par Des Agents Chimiques A L'Action Des Radiations et Des Cytostatiques," Rev. Roum. Biochim., 8:117–122 (1971).

Vivants Par Des Agents Chimiques A L'Action Des Radiations et Des Cytostatiques, Rev. Roum. Bioshim., 8:117–122 (1971).

Omura, et al., "Relationship Between the Structures of Fatty Acid Amide Derivatives and Their Antimicrobial Activities," Antimicrobial Agents and Chemotherapy, 6:207–215 (1974).

Nery et al., "Isolation and Partial Characterization of Macromolecular Urinary Aggregates Containing Carcinoembryonic Antigen–Like Activity," British Jour. of Cancer (1974) 413–424.

Schroering, et al., "Fatty Acid Synthetase In Chemically Induced Mammary Carcinomas", Res. Communications In Chem. Path. and Pharmocology, (1974) 9:775–778.

Lin, et al., "Fatty Acid Synthetase from a Mouse Mammary Adenocarcinoma", Cancer Research, (1975) 35:3094–3099.

Abraham, et al., "Lipids and Lipogenesis in a Murine Mammary Neoplastic System", in Control Mechanisms in Cancer, Criss, et al eds., pp. 363–378, Raven Press, NY (1976).

Omura, Satoshi, "The Antibiotic Cerulenin, a Novel Tool for Biochemistry as an Inhibitor of Fatty Acid Synthesis," Bacteriological Reviews, 40:681–697 (1976).

Pitot, et al., "Contribution of the Morris Hepatomas to the Biochemistry of Cancer–Establishment of the Phenotypic Heterogeneity of Neoplasms In Vivo", Progress In Cancer Res. And Therapy, (1976) 1:21–37.

Altenbern, Robert A., "Extreme Sensitivity of Staphylococcal Enterotoxin B and C Production to Inhibition by Cerulenin," Antimicrobial Agents and Chemotherapy, 11:906–908 (1977).

Altenbern, Robert A., "Cerulenin–Inhibited Cells of *Staphylococcus aureus* Resume Growth When Supplemented with Either a Saturated or an Unsaturated Fatty Acid," Antimicrobial Agents and Chemotherapy, 11:574–576 (1977).

(List continued on next page.)

*Primary Examiner*—Keith D. Hendricks
*Attorney, Agent, or Firm*—Baker & Botts, L.L.P.

[57] ABSTRACT

Fatty acid synthase (FAS) is overexpressed in carcinomas with poor prognosis, but little FAS expression is identified in normal tissues Inhibition of fatty acid synthesis is selectively toxic to carcinoma cells, while normal cells with low FAS activity are resistant. This invention provides a method of treating cancer patients where fatty acid synthesis by cells of the patient's tumor is inhibited with resultant interruption of the disease process.

40 Claims, 25 Drawing Sheets

OTHER PUBLICATIONS

Partida, et al., "Comparative Effects of Diphenylglioxal and its Superoxide on Experimental Tumors," Arch. de Farmacol. y Toxicol., III:231–240 (1977).

Chen, et al., "The Cerulenin–Induced Formation of 1–Acyl–Lysophosphatidyl Glycerol in *Bacillus Megaterium*," Biochemical and Biophysical Research Communications, 80:126–132 (1978).

Javid et al., "Human Haptoglobins," Curr. Topics in Hematology, (1978), 1:151–192.

Carson, et al., "Effect of Cerulenin on *Streptococcus faecalis* Macromolecular Synthesis and Cell Division," Journal of Bacteriology, 133:472–476 (1978).

Cooper et al., "Acute Phase Reactant Proteins in Cancer," Advances in Cancer Research, (1979), 30:1–44.

Ahmad, et al., "Increase in Fatty Acid Synthetase Content of 3T3–L Cells Undergoing Spontaneous and Chemically Induced Differentiation to Adipocytes", Biochem. J. (1979) 182:509–514.

Caulfield, et al., "Export of Extracellular Levansucrase by *Bacillus subtilis*: Inhibition by Cerulenin and Quinacrine," Journal of Bacteriology, 138:345–351 (1979).

O'Brien et al., "Qualitative Analysis of Proteinuria Associated with Bladder Cancer," Investigative Urology, (1979), 17:28–32.

Folkersen et al., "Affinity Chromatographic Purification of a New High Molecular Weight Pregnancy Specific Protein–SP–4," Carcino–Embryonic Proteins (1979), 2:503–508.

Davis et al., "Reactions with Simple Haptens," Microbiology, 3rd Ed., Harper & Row, pp. 298–306 (1980).

Leung, et al., "Streptococcus mutans Dextransucrase: Effect of Cerulenin on Lipid Synthesis and Enzyme Production," Infection and Immunity, 28:846–852 (1980).

Sutcliffe et al., "Studies on Human Pregnancy–Associated Plasma Protein A," Biochem. Jour. (1980), 191:799–809.

Smith, et al., "Thioesterase II, a New Marker Enzyme for Human Cells of Breast Epithelial Origin," JNCI, 73:323–328 (1981).

Thompson, et al., "Purification and Properties Of Fatty Acid Synthetase From A Human Breast Cell Line", Biochim. Biophys. Acta, 662:125–130 (1981).

Carson, et al., "Effect of Cerulenin on Cellular Autolytic Activity and Lipid Metabolism During Inhibition of Protein Synthesis in *Streptococcus faecalis*," Journal of Bacteriology, 146:590–604 (1981).

Bocquet–Pages, et al., "Lipid–Synthesis–Dependent Biosynthesis (or Assembly) of Major Outer–Membrane Proteins of *Escherichia coli*," Eur. J. Biochem., 118:105–111 (1981).

Omura, Satoshi, Chapter 39 "Cerulenin" in Methods in Enzymology, 72:520–532, 1981.

Ahmad, et al., "Inactivation of Rat Mammary Gland Fatty Acid Synthetase By S–(4–bromo–2,3–dioxobutyl)–Coenzyme", Fed. Proc. (1981) 40:1794 Abstract 1463.

Mäntsälä, et al., "Secretion of β–lactamase by *Escherichia coli* in vivo and in vitro: Effect of Cerulenin," Antonie van Leeuwenhoek, 48:353–364 (1982).

Thompson, et al., "Lack of Coordinated Regulation Of Lipogenic Enzymes In A Human Breast Cell Line SKBr3", Biochim. Biophys. Acta, 712:217–220 (1982).

Clements, et al., "Irreversible Inhibition of Fatty Acid Synthase from Rat Mammary Gland with S–(4–bromo–2,3–dioxobutyl)–CoA", Biochem. J. (1982) 207:291–296.

Ahmad, et al., "Studies on Acetyl–CoA Carboxylase and Fatty Acid Synthase from Rat Mammary Gland and Mammary Tumors", Biochem. J. (1982) 208:443–452.

Hayashi, et al., "Mechanism of Action of the Antibiotic Thiolactomycin Inhibition of Fatty Acid Synthesis of *Escherichia Coli*," Biochem. Biophys. Res. Comm., 115:1108–1113 (1983).

Baseler et al., "Purification of Haptoglobin and Its Effects on Lymphocyte and Alveolar Macrophage Responses," Inflammation, (1983), 7:387–400.

Haram et al., "Serum Protein Pattern in Normal Pregnancy with Special Reference to Acute –Phase Reactants," British Jour. of Obstetrics and Gynaecology (1983), 90:130–145.

Kuhajda et al., "The Distribution of Carcinoembryonic Antigen in Breast Carcinoma," Cancer (1983), 52:1257–1264.

Mendoza, et al., "Thermal Regulation of Membrane Fluidity in *Escherichia coli*," J. Biol. Chem., 258:2098–2101 (1983).

Spiegelman, et al., "Fibronectin Modulation of Cell Shape and Lipogenic Gene Expression in 3T2–Adipocytes", Cell (1983) 35:657–666.

Mahajan, et al., "Cerulenin Inhibition of Lipid Synthesis and Its Reversal by Exogenous Fatty Acids in *Mycobacterium smegmatis* ATTC 607," Can. J. Biochem. Cell Biol., 63:85–90 (1984).

Mahajan, et al., "Cerulenin Effect on Phospholipid Metabolism in *Mycobacterium Smegmatis* ATTC 607," Biochemica et Biophysica Acta, 795:493–498 (1984).

Bischof, "Placental Proteins," Contributions to Gynecology and Obstetrics (1984), 12:1–5 and 41–74.

Maeda et al., "Duplication Within the Haptoglobin $Hp^2$ Gene," Nature, (1984),309:131–135.

Schindler et al., "Histochemical Localization of Pregnancy–Associated Plasma A in Fetal, Infant, and Adult Organs and Comparison Between Antisera," Gynecol. Obstet. Invest. (1984), 18:88–94.

Bischof, "Placenta Proteins," Contributions to Gynecology and Obstetrics (1984), 12:46–55.

Kuhajda et al., "Pregnancy–Specific Beta–1 Glycoprotein (SP–1) in Breast Carcinoma," Cancer (1984), 54:1392–1396.

Maeda, "Nucleotide Sequence of the Haptoglobin and Haptoglobin–Related Gene Pair," Jour. of Biol. Chem., (1985), 260:6698–6709.

Bensi et al., "Structure and Expression of the Human Haptoglobin Locus," The EMBO Journal, (1985) 4:119–126.

Kuhajda et al., "Pregnancy–Associated Plasma Protein A:A Clinically Significant Predictor of Early Recurrence in Stage I Breast Carcinoma is Independent of Estrogen Receptor Status", Am. J. Pathol. (1985), 121:342–348.

Kuhajda et al., "Pregnancy–Associated Plasma Protein A:A Clinically Significant Predictor of Early Recurrence in State II Breast Carcinoma," Hum. Pathol. (1985), 16:228–235.

Ceriani, et al., "Immunohistochemical Studies In Breast Cancer Using Monoclonal Antibodies Against Breast Epithelial Cell Components and With Lectins", Devel. Oncol., (1985) 34:233–63.

Hait, et al., "Inhibition of Growth of Leukemic Cells by Inhibitors Of Calmodulin: Phenothiazines and Melittin," Cancer Chemother. Pharmacol., 14:202–205 (1985).

Pawlak, et al., "Evaluation of Thioesterase II as a Serum Marker for Rat Mammary Cancer," Cancer Research, 46:4712–4719 (1986).

Nishida, et al., "Effect of Thiolactomycin on the Individual Enzymes of the Fatty Acid Synthase System in *Escherichia coli*," J. Biochem., 99:1447–1454 (1986).

Hoberg, et al., "Characterization of Cerulenin–Resistant Mutants of *Candida albicans*," Infection and Immunity, 51:102–109 (1986).

Mowles et al., "A Two–Site Immunoradiometric Assay for Human Pregnancy–Associated Plasma Protein A (PAPP–A) Using Monoclonal Antibodies", Journal of Immunological Methods, (1986) 95:129–133.

Maeda et al., "Polymorphisms in the Human Haptoglobin Gene Cluster: Chromosomes with Multiple Haptoglobin-–Related (Hpr) Genes," Proc. Natl. Acad. Sci. USA (1986), 83:7395 7399.

Chemnitz et al., "Comparison of Different Antibody Preparations Against Pregnancy–Associated Plasma Protein–A (PAPP–A) for Use in Localization and Immunoassay Studies," Br. Jour. of Obstetrics and Gynaecology (1986), 93:916–923.

Fujii, et al., "Effect of Cerulenin, an Inhibitor of Fatty Acid Synthesis, on the Immune Cytolysis of Tumor Cells", Jap. Jap. J. Exp. Med., 56:99–106 (1986).

Chalbos, et al., "Cloning of cDNA Sequences of a Progestin-–Regulated mRNA from MCF7 Human Breast Cancer Cells", Nucl. Acids Res., 14:965–981 (1986).

Abraham, et al., "Lipid Metabolism and Enzyme Activities In Hormone–Dependent and Hormone–Independent Mammary Adenocarcinoma in GR Mice", JNCI (1986) 77:233–239.

Weiss, et al., "Fatty–Acid Biosynthesis in Man, a Pathway of Minor Importance", Biol. Chem. Hoppe–Seyler, (1986) 367:905–912.

Oh et al., "An Analogy Between Fetal Haptoglobin and a Potent Immunosuppressant in Cancer," Cancer Res., (1987), 47:5120–5126.

Thompson et al., "Elevated Levels of Abnormally–Fucosylated Haptoglobins in Cancer Sera," British Journ. of Cancer, (1987), 56:605–610.

Kuhajda et al., "Molecular Characterization of a Human Breast Cancer Antigen Predicting Early Relapse," Lab. Invest. (1987) vol. 56, Abstract 236.

Chalbos, et al., "Fatty Acid Synthetase and Its mRNA Are Induced By Progestins in Breast Cancer Cells", (1987) J. Biol. Chem., 262:9923–9926.

Bolla, et al., "The Assembly of the Major Outer Membrane Protein OmpF of *Escherichia coli* Depends on Lipid Synthesis," The EMBO Journal, 7:3595–3599 (1988).

Harris, et al., "Inhibition of Phenolic Glycolipid–1 Synthesis in Extracellular *Mycobacterium leprae* as an Indicator of Antimicrobial Activity," International Journal of Leprosy, 56:588–591 (1988).

DAKO Corporation, Technical Information and Product List regarding anti–PAPP–A antiserum (1988).

McAllister, et al., "The Effect of Tumour Growth on Liver Pantothenate, CoA, and Fatty Acid Synthetase Activity in the Mouse", Br. J. Cancer (1988) 57:83–86.

Tisdale, et al., "Changes in Host Liver Fatty Acid Synthase in Tumour–Bearing Mice", Cancer Letters (1988) 42:231–235.

Wilder, et al., "Altered Rate and Fatty Acid Distribution in Adriamycin (P388A) Cells", Proceedings of AACR, (1988) 29:318 Abstr. 1265.

Wall, et al., "Covalent Reaction of Cerulenin at the Active Site of acyl–CoA Reductase of *Photobacterium phosphoreum*," Biochem. Cell Biol., 67:163–167 (1989).

Joyeux, et al., "Progestin Increases Gene Transcription and Messenger Ribonucleic Acid Stability of Fatty Acid Synthetase in Breast Cancer Cells," Molecular Endocrinology, 4:681–686 (1989).

Byers, et al., "Inhibition of *Vibrio harveyi* Bioluminescence by Cerulenin: In Vivo Evidence for Covalent Modification of the Reductase Enzyme Involved in Aldehyde Synthesis," Journal of Bacteriology, 171:3866–3871 (1989).

Bueler et al., "Antiserum to Pregnancy–Associated Plasma Protein A (PAPP–A) Recognizes Human Haptoglobin", Br. J. Ob. Gyn., (1989), 96:867–869.

Pasternack, et al., "Expression of Haptoglobin–related Protein (Hpr) Epitopes In Human Breast Carcinoma Correlates With Increased Phenotypic Malignancy", J. Cell. Biochem., 13B:137, Abstr. E410 (1989).

Shurbaji, et al., "Immunohistochemical Expression of Hpr In Primary And Metastatic Breast Carcinoma", Lab. Invest., 60:1, Abstr. 525 (1989).

Spydevold, et al., "Activities of Enzymes of Lipid Metabolism in Morris Hepatoma", Biochimica et Biophysica Acta (1989) 1003:80–83.

Funabashi, et al., "Binding Site of Cerulenin in Fatty Acid Synthetase," (1989) J. Biochem., 105:751–755.

Oh, et al., "Monoclonal Antibody to SER Immune Suppressor Detects Polymeric Forms of Haptoglobin," (1989) Hybridoma, 8:449–466.

Romanens, et al., "Cac'ing Safer with Cac'ing Spawning," Der Champignon, 1989, pp. 22–30.

Chambon, et al., "Progestins and Androgens Stimulate Lipid Accumulation In T47D Breast Cancer Cells Via Their Own Receptors", J. Steriod Biochem., 33:915–922 (1989).

Kuhajda et al., "Expression of Haptoglobin–Related Protein and its Potential Role as a Tumor Antigen", Proc. Natl. Acad. Sci. USA (1989), 86:1188–1192.

Kuhajda et al., "Haptoglobin–Related Protein (Hpr) Epitopes in Breast Cancer as a Predictor of Recurrence of the Disease", N. Eng. J. Med. (1989) 321:636–641.

Hourdou, et al., "Specific Inhibition of Iturin Biosynthesis by Cerulenin," Can. J. Microbiol., 36:164–168 (1990).

Amy, et al "Molecular Cloning of the Mammalian Fatty Acid Synthase Gene and Identification of the Promoter Region," Biochem. J., 271:675–679 (1990).

Ried, et al., "Role of Lipopolysaccharide in Assembly of *Escherichia coli* Outer Membrane Proteins OmpA, OmpC, and OmpF," Journal of Bacteriology, 172:6048–6053 (1990).

Chalbos, et al., "Expression of the Progestin–Induced Fatty Acid Synthetase in Benign Mastopathies and Breast Cancer as Measured by RNA in Situ Hybridiazation", JNCI, 82:602–606 (1990).

Escot, et al., "Regulation of Fatty Acid Synthetase Ribonucleic Acid In The Human Endometrium During the Menstrual Cycle", J. Clin. Endocrinol. Metab. 70:1319–1324 (1990).

Joyeux, et al., "Effects of Progestins and Menstrual Cycle on Fatty Acid Synthetase And Progesterone Receptor in Human Mammary Glands", J. Clin. Endocrinol. Metab., 70:1438–1444 (1990).

Chalbos, et al., "Progestin–Induced Fatty Acid Synthetase in Breast Cancer", Ann. N. Y. Acad. Sci., 1990, vol. 595, pp. 67–73.

Fawcett, et al., "Identification of the Products of the Haptoglobin–Related Gene," Biochim Biophys. Acta, (1990) 1048:187–193.

Shurbaji, et al., "Expression of Haptoglobin Related Protein (Hpr) Epitopes By Prostate Carcinoma: A Potential Prognostic Indicator", Intl. Acad. Pathol. Mtg., Mar. 1991, Abstr. 300.

Ziegler, et al., "Current Status of Adjuvant Therapy of Early Breast Cancer", Am. J Clin. Oncol., 14:101–110 (1991) (Abstract only).

Corrigan, et al., "Prognostic Value of the Immunohistochemical Demonstration of Haptoglobin-Related Protein in Breast Cancer", A.J.C.P., Sep. 1991, p. 406, Abstr. 19.

Shurbaji, et al., "Expression of Oncogenic Antigen 519 (OA-519) in Prostate Cancer Is A Potential Prognostic Indicator", Am. J. Clin. Pathol., 97:686–691 (1992).

"Cancer Test Nearing Market", The Daily Record, Oct. 3, 1991, pp. 3, 5.

"In Vitro Cancer Diagnostics", BioWorld Today, Oct. 7, 1991, pp. 3.

"New Cancer Analytes: Finally, the Silver Bullet?", The Genesis Report, Dec. 1991/Jan. 1992, pp. 10–12.

Chalbos, et al., "The Anti-progestin RU486 Stabilizes the Progestin-induced Fatty Acid Synthetase mRNA but Does Not Stimulate Its Transcription", J. Biol. Chem., 266:8220–8224 (1991).

Redston, et al., "Expression of OA519 (Haptoglobin-Related Protein Epitopes) In Colorectal Carcinomas: Comparison With Molecular Genetic Alterations and Metastsis", Lab. Invest., 66:13A (1992), Abstr. 66.

Cote, et al., "Prognostic Features In Breast Carcinoma: Detection Of Occult Axillary Lymph Node Micrometastases (LNM), Expression of Haptoglobin Related Binding Protein (OA519) And Progesterone Receptor (PR) in Primary Tumors", Lab. Invest., 66:47A (1992), 77 Abstr. 272.

Cote, et al., "Expression of OA519 (Haptoglobin-Related Protein Epitopes) In Colorectal and Carcinomas: Comparison With Molecular Genetic Alterations and Metastasis", Lab Invest., 66:47A (1992), Abst. 272.

Martin, et al., "Immunohistochemical Expression of OA-519 In Pre-Neoplastic and Neoplastic Lesion Polyps of the Colon," American Society for Clinical Oncology, (Abstract).

Ookhtens et al., "Liver and adipose tissue contributions to newly formed fatty acids in an ascites tumor," Am. J. Physiol. 247 (Regulatory Integrative Comp. Physiol.) R–146–R153, 1984.

Shimada et al., "Ring–Opening Aldol–Type Reaction of 2,2–Dialkoxycyclopropanecarboxylic Esters with Carbonyl Compounds. 3. The Diastereoselective Synthesis of 2,3,4-Trisubstituted γ–Lactones," Journal of Organic Chemistry, vol. 58, No. 19, pp. 5226–5234, 1993.

Murta et al., "Synthesi and Absolute Stereochemistry of (−)–Protolichesterinic Acid, Antitumor Antibiotic Lactone from *Cetraria islandica*," Journal of Organic Chemistry, vol. 58, No. 26, pp. 7537–7541, 1993.

Park et al., "Methylenolactocin, A Novel Antitumor Antibiotic from *Penicillium* Sp.," The Journal of Antibiotics, vol. XLI, No. 6, pp. 751–758, Jun. 1988.

de Azevedo et al., "Novel, Enantioselective Lactone Construction. First Synthesis of Methylenolactocin, Antituor Antibiotic from *Penicillium* sp.," Journal of Organic Chemistry, vol. 57, No. 17, pp. 4567–4569, 1992.

Funabashi et al (1989) J. Biochem 105, 751–755.

Clements et al. (1982) Biochem J 207, 291–296.

Abraham et al (1975) in "Control Mechanisms in Cancer" (Criss et al., Eds) Raven Press, New York, 363–378.

Tomada et al (1987) Biochem Biophys Acta 921, 595–598.

Tomada et al (1981) J. Biol Chem 266, 4214–4219.

Ahmad et al (1982) Biochem J. 208, 443–452.

Weiss et al (1986) Biol. Chem Hopp–Seyler 367, 905–912.

Chalbos et al (1990) J. Natl Can. Inst. 82, 602–606.

Chalbos et al (1987) J. Biol. Chem. 262, 9923–9926.

Schroerinj et al (1974) Res. Comm. Chem. Path Pharm. 9, 775–778.

Fujii et al (1986) Jpn. J. Exp. Med. 56, 99–106.

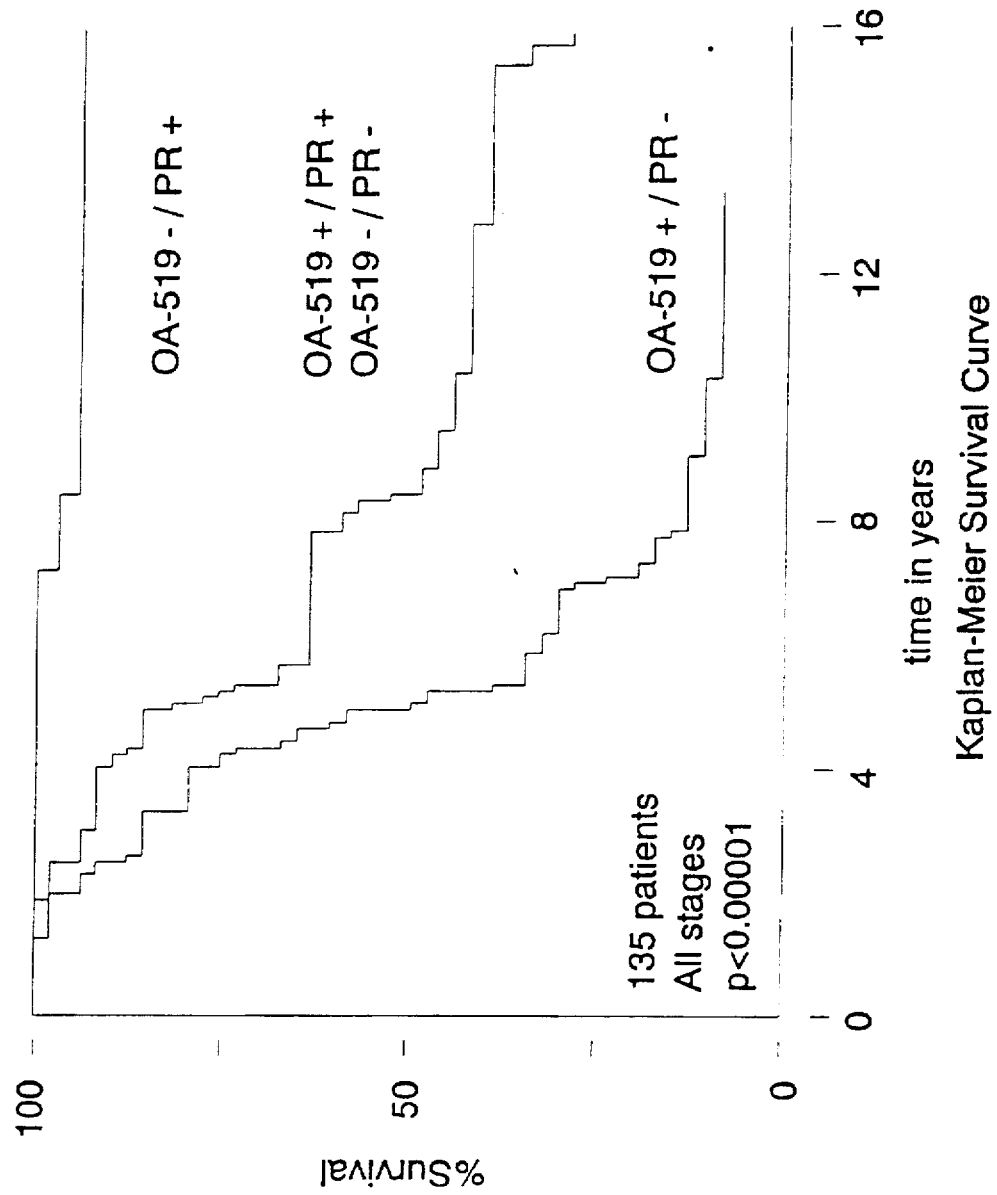

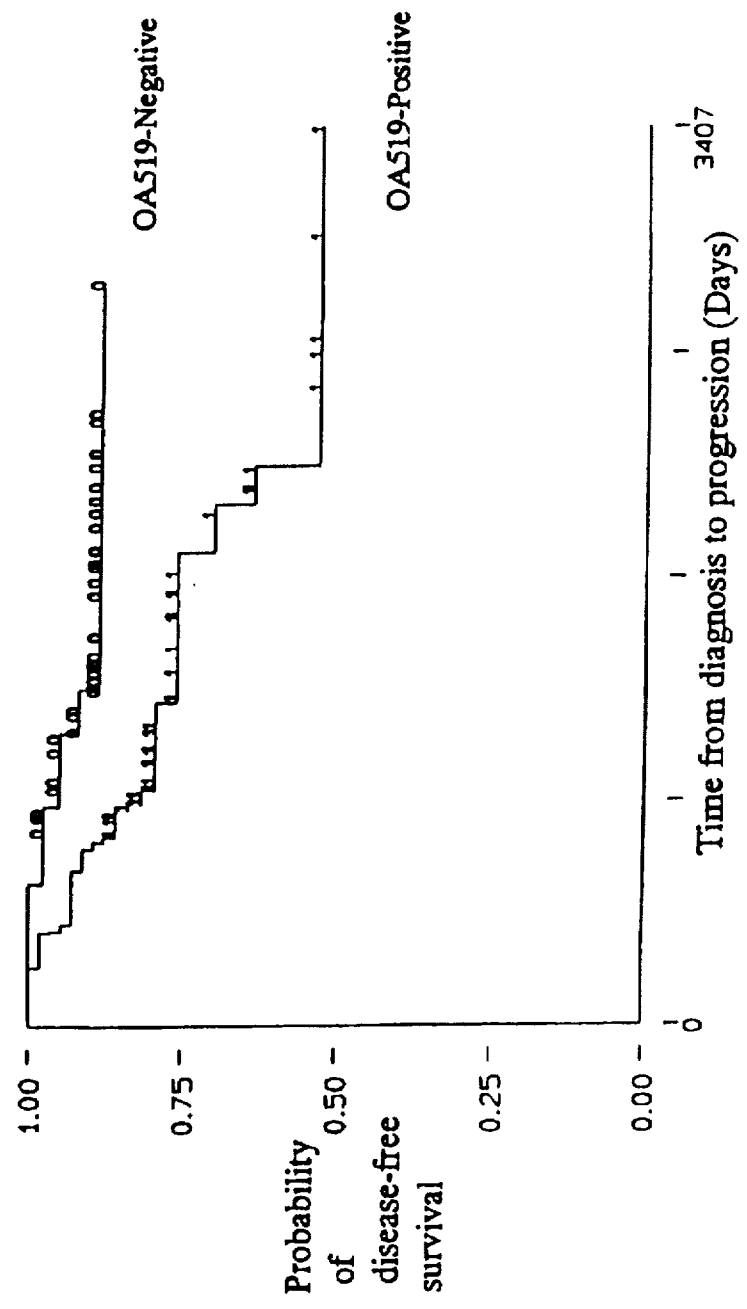
FIGURE 2A: KAPLAN-MEIER PLOT OF THE DISEASE FREE INTERVAL IN PATIENTS WITH PRIMARY PROSTATE CANCER

OA-519 EXPRESSION AND PROGNOSIS IN OVARIAN CARCINOMA

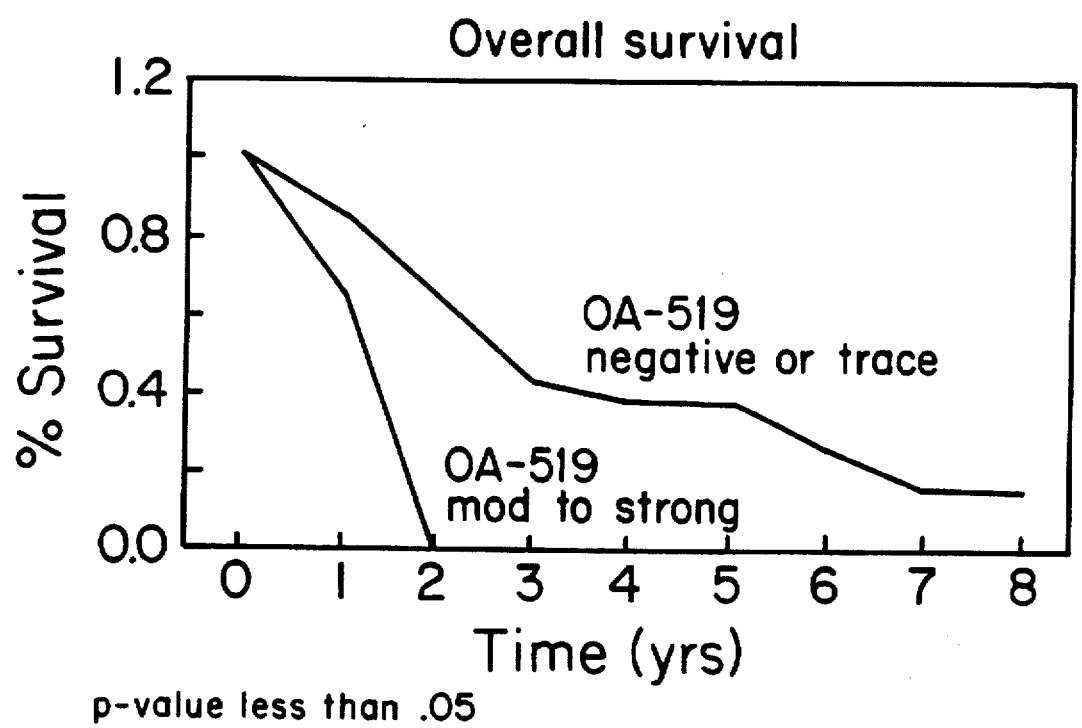
FIGURE 2B(ii)

Figure 3A: 34-Amino Acid Sequence of a Peptide Immunologically Cross-Reactive with OA-519 leu tyr ser gly asn asp val thr asp ile ser asp asp arg phe pro lys pro pro glu ile ala asn gly tyr val glu lys leu phe arg tyr gln cys.

Figure 3B: OA-519 Peptide Sequence Analysis

Sequence 1: Analysis of 134 kD OA-519 peptide sequence homology.

OA-519 peptide sequence:                LQQHDVAQEQWXP
```
                                         ||||||| :||:|
```
Rat fatty acid synthase (EC 2.3.1.85):  TKLQQHDVAQGQWDPSGPAPTNLGALD
                                                1290         1300

84.6% identity in 13 amino acid overlap.

Sequence 2: Analysis of OA-519 peptide sequence from Example 12
of the Continuation-In-Part of U.S. Serial No. 07/735522 filed July 26, 1991.

OA-519 peptide sequence:                HAVVLE
```
                                         ||||||
```
Rat fatty acid synthase (EC 2.3.1.85):  HAVVLE 100% identity in 6 amino acid overlap.

Figure 5: Dixon Plot of Cerulenin Inhibition of Fatty Acid Synthase Activity

Figure 6: Cerulenin Induces Selective Growth Inhibition of Human Mammary Cancer Cells Compared to Normal Human Fibroblasts Figure 7a: Correlation Between FAS Activity and Cell Growth Inhibition by Cerulenin Figure 7b: Key for Human Cell Lines from Figure 7a Human Carcinoma Cell Lines:

Mammary: HS578t
                 ZR-75-1
                 MCF-7
                 MCF-7a (adriamycin resistant)

Lung: H125
             H157
             U1752

Prostate: DU145
                 LNCAP

Colon: SW480

Normal Human Cells: Fibroblasts

Figure 8: Correlation of Fatty Acid Synthase (FAS) Activity and Total Fatty Acid Biosynthesis

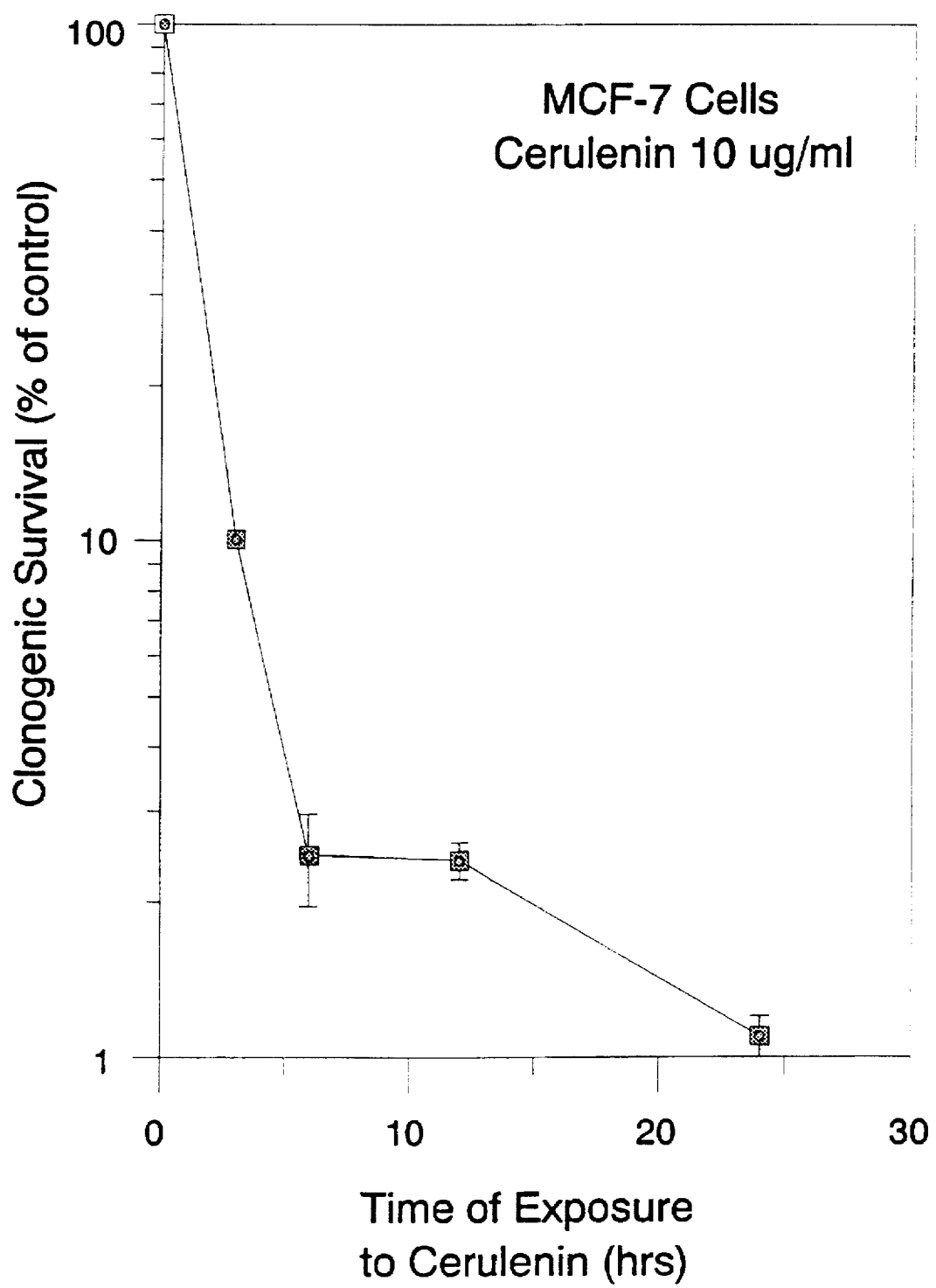
Figure 11A: Effect of Cerulenin on Clonogenic Survival of Human Mammary MCF-7 Cells

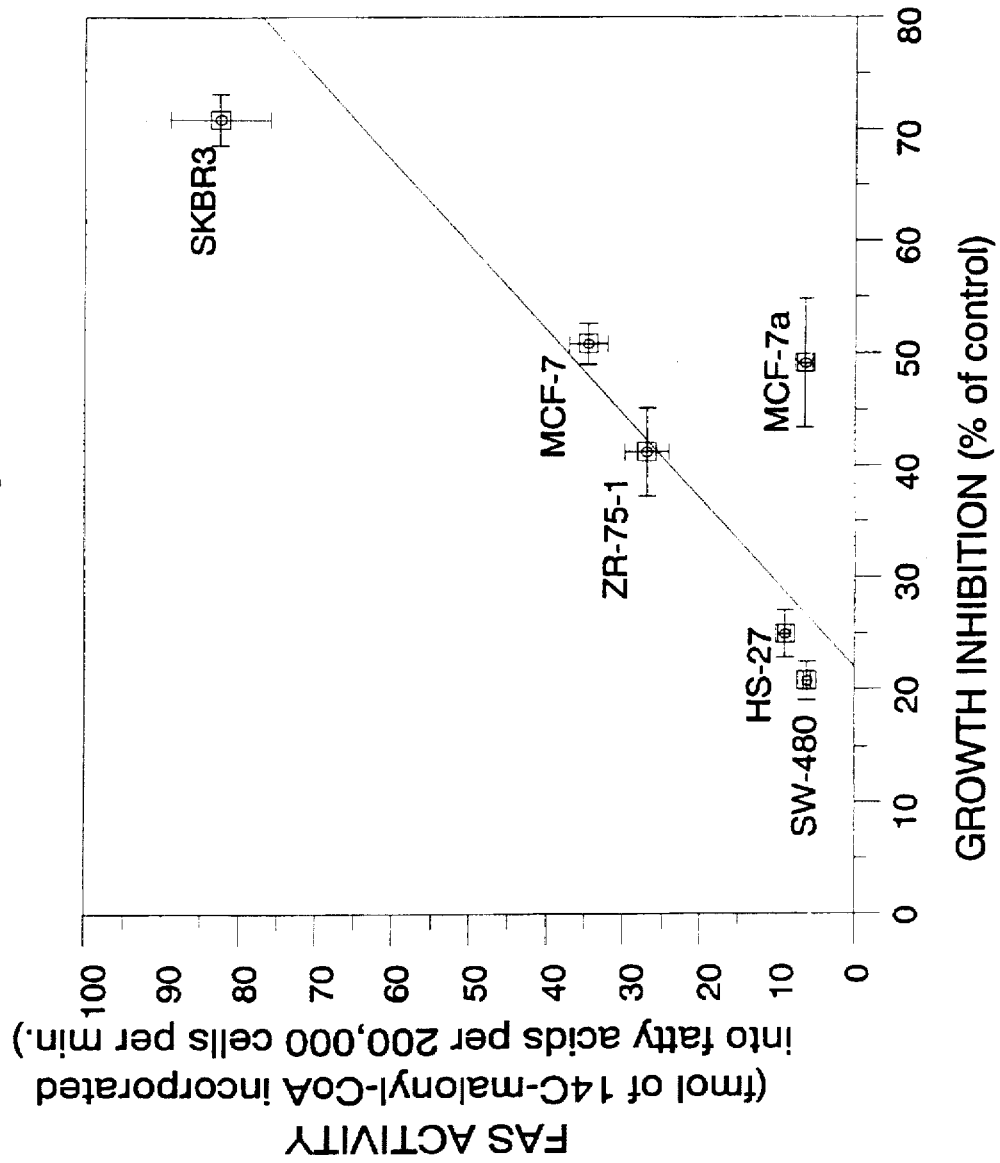
Figure 11B: Correlation Between FAS Activity and Degree of Cell Growth Inhibition by Cerulenin

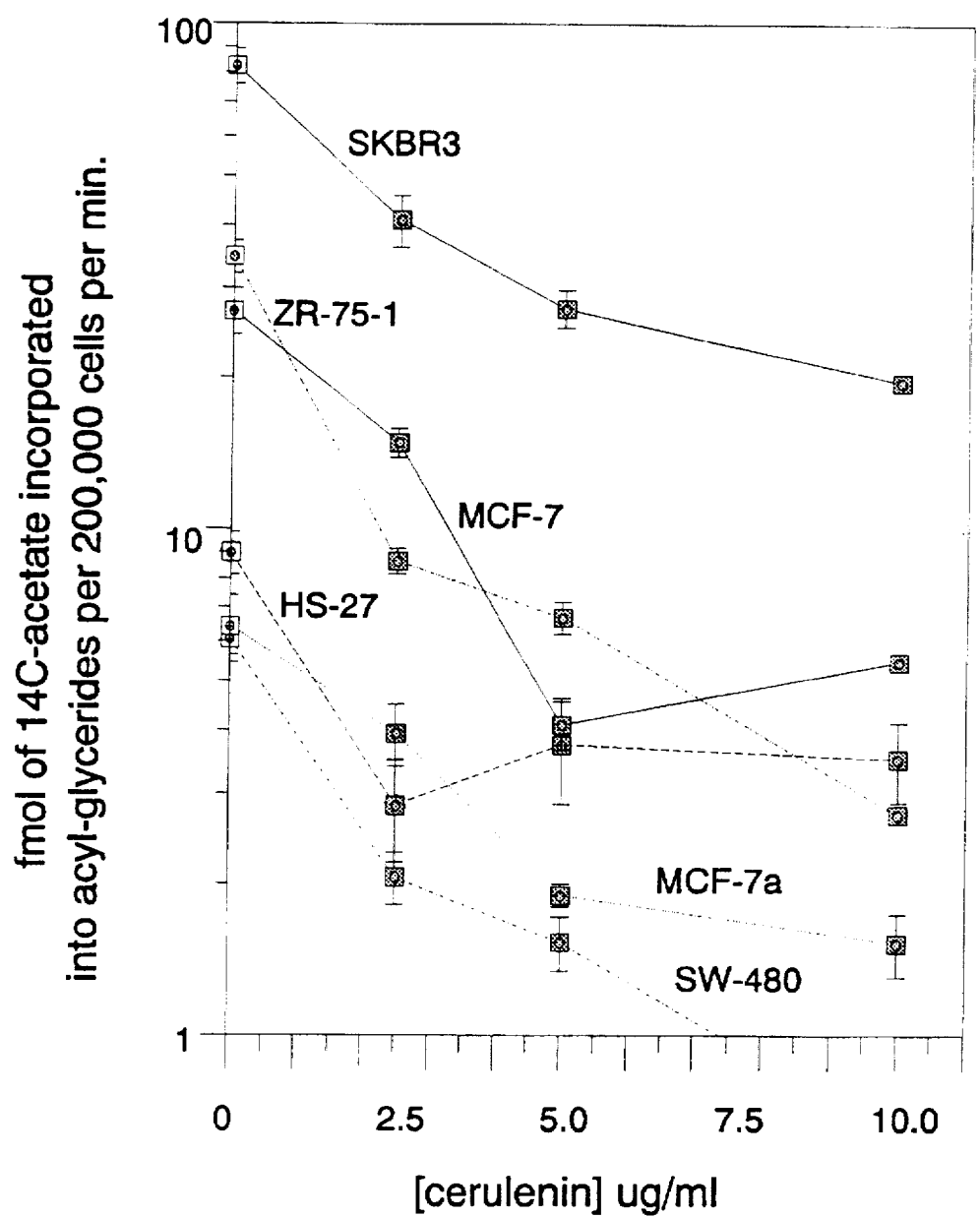
Figure 12A: Cerulenin Inhibits 14C-acetate Incorporation into Acyl Glycerides

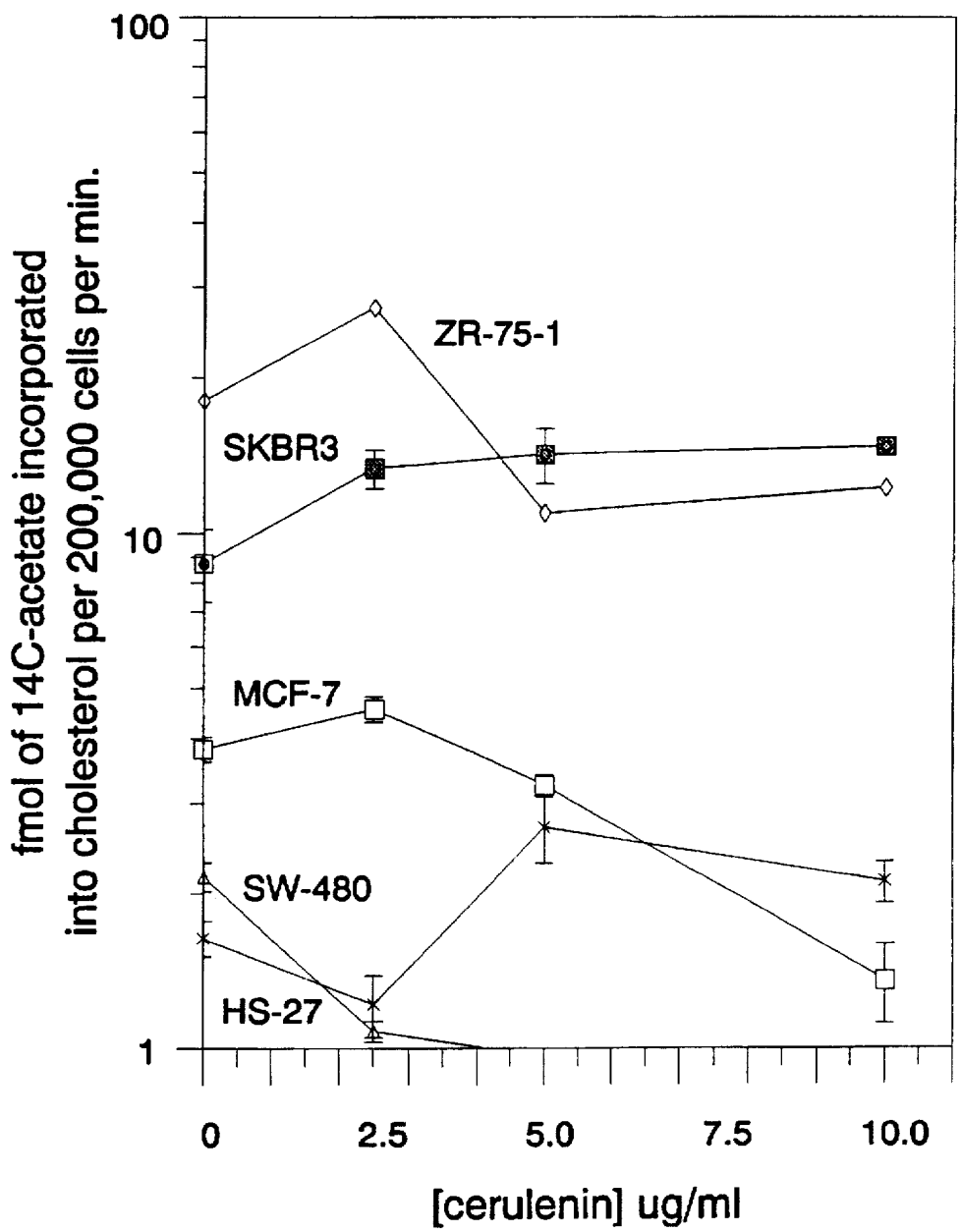
Figure 12B: Cerulenin Does Not Significantly nor Consistently Alter 14C- acetate Incorporation into Cholesterol

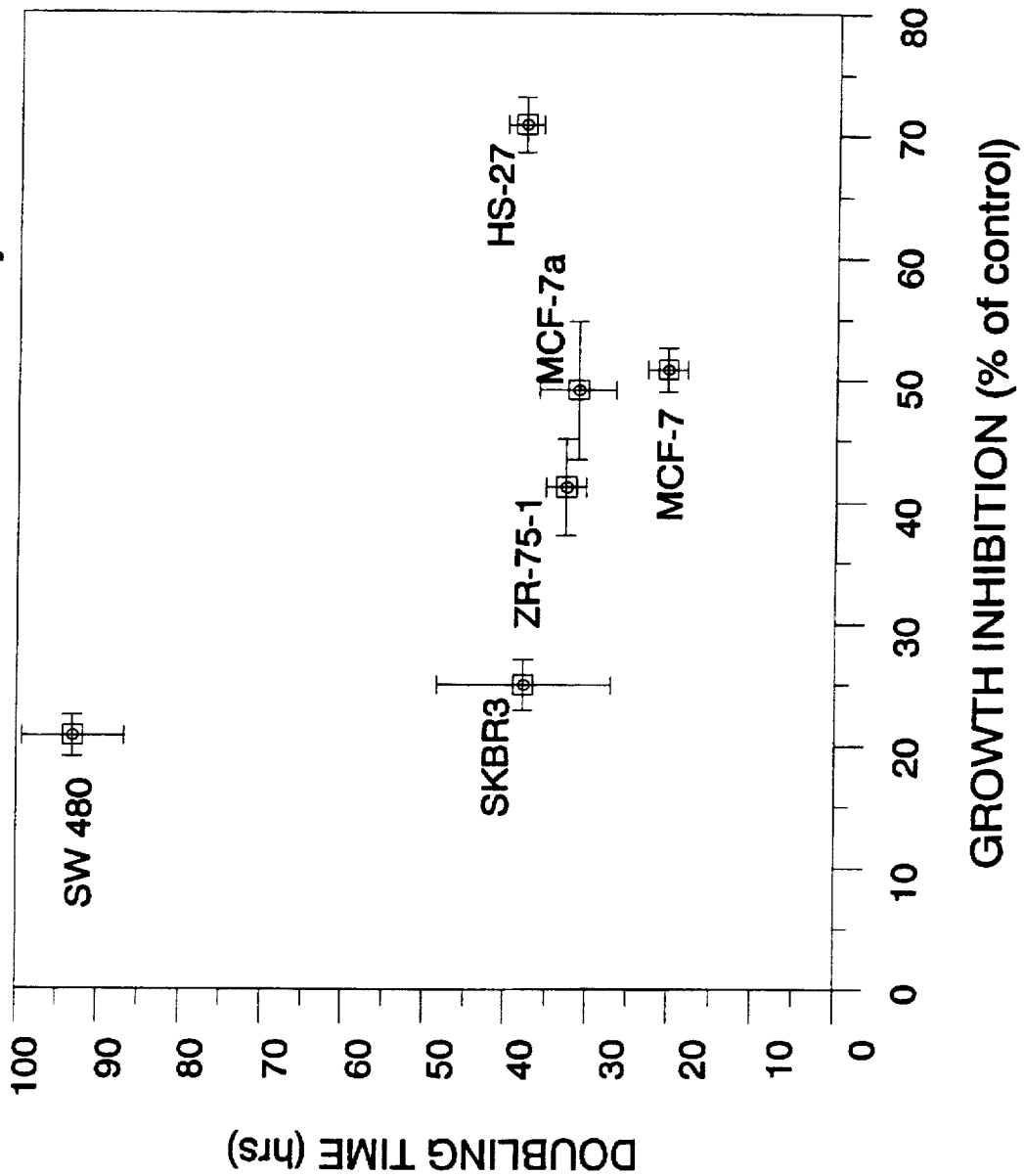
Figure 13: Lack of Correlation Between Cell Doubling Times and Degree of Growth Inhibition by Cerulenin

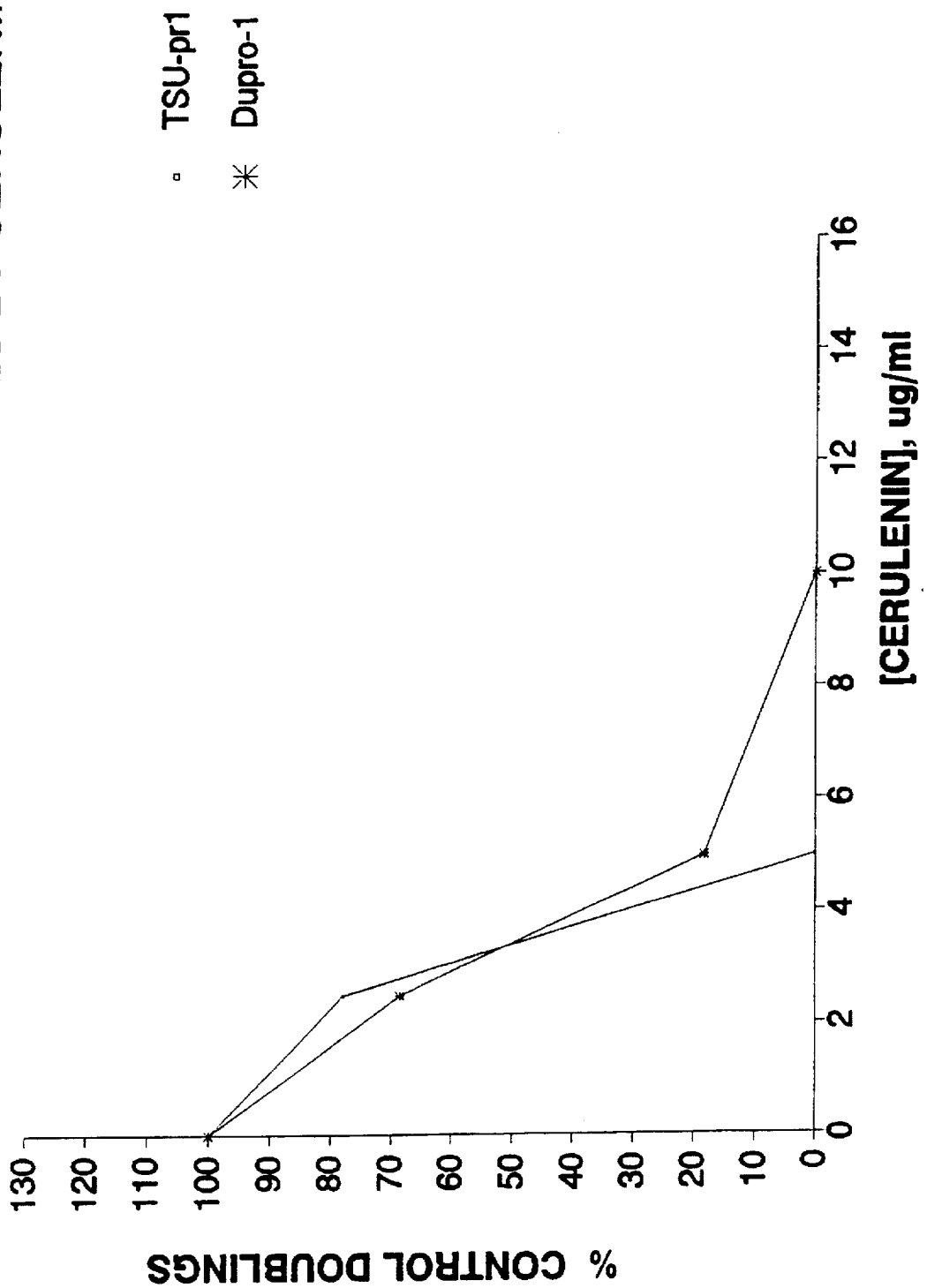

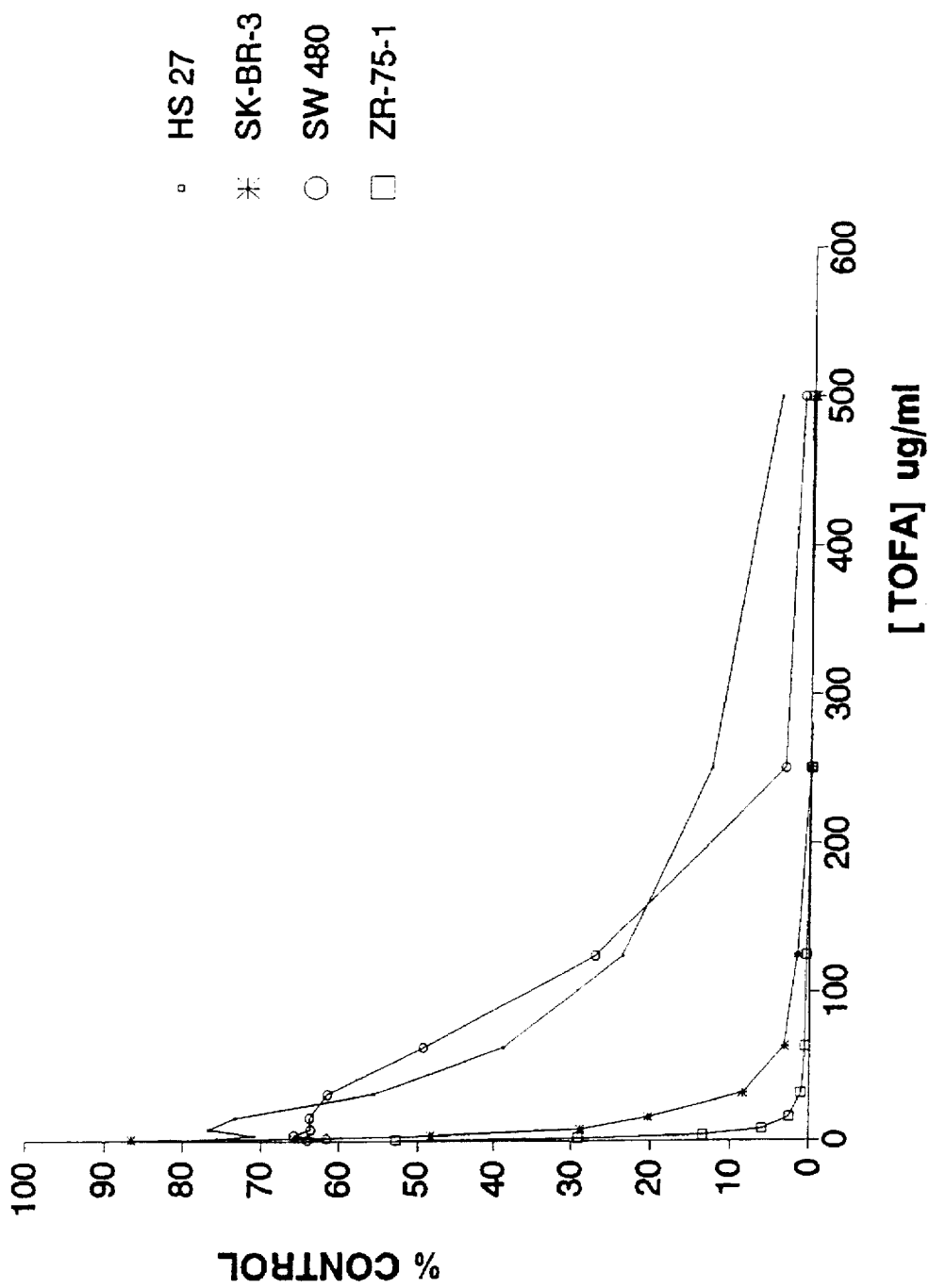

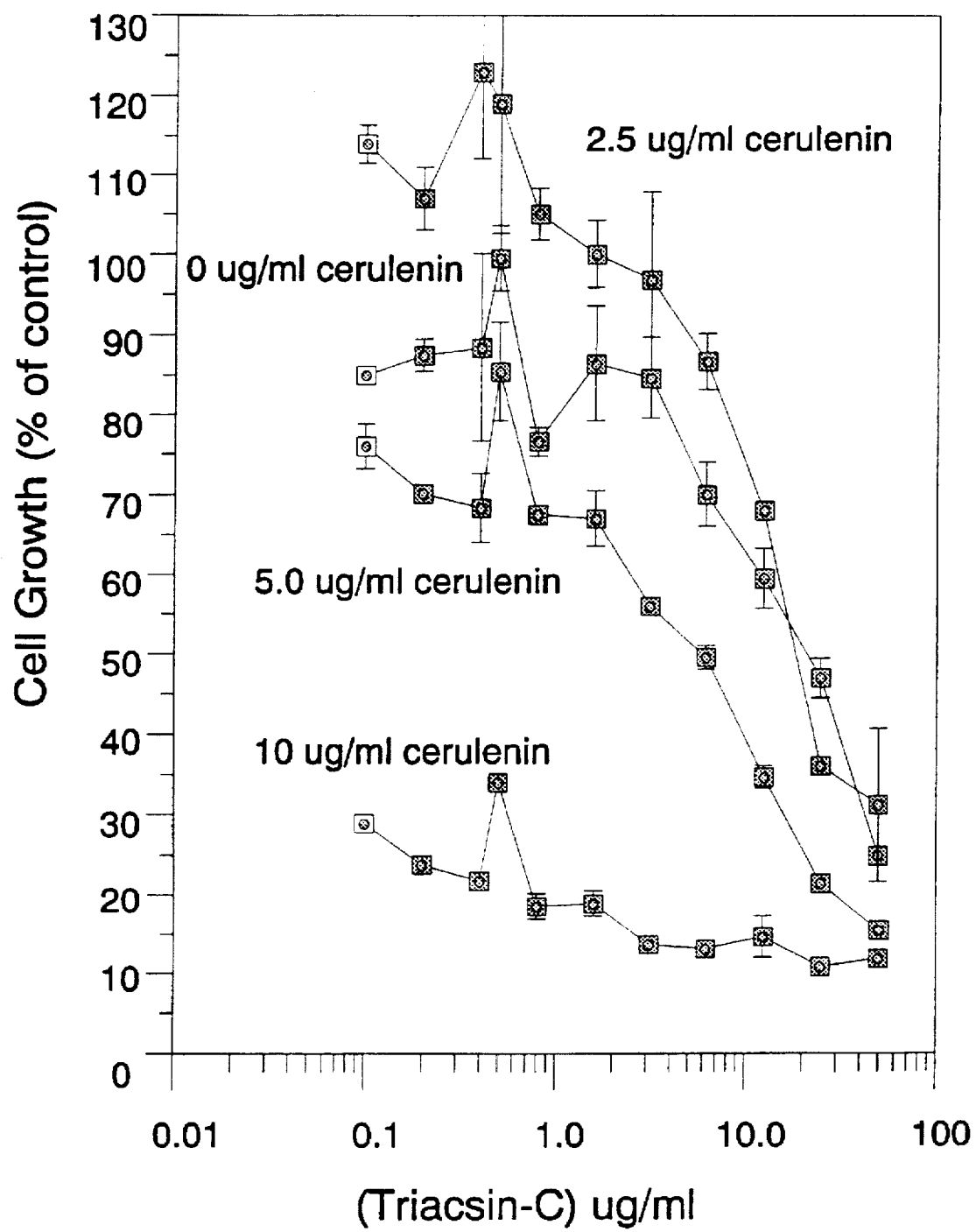
Figure 16: Cerulenin Increases Degree of Growth Inhibition by Triacsin-C

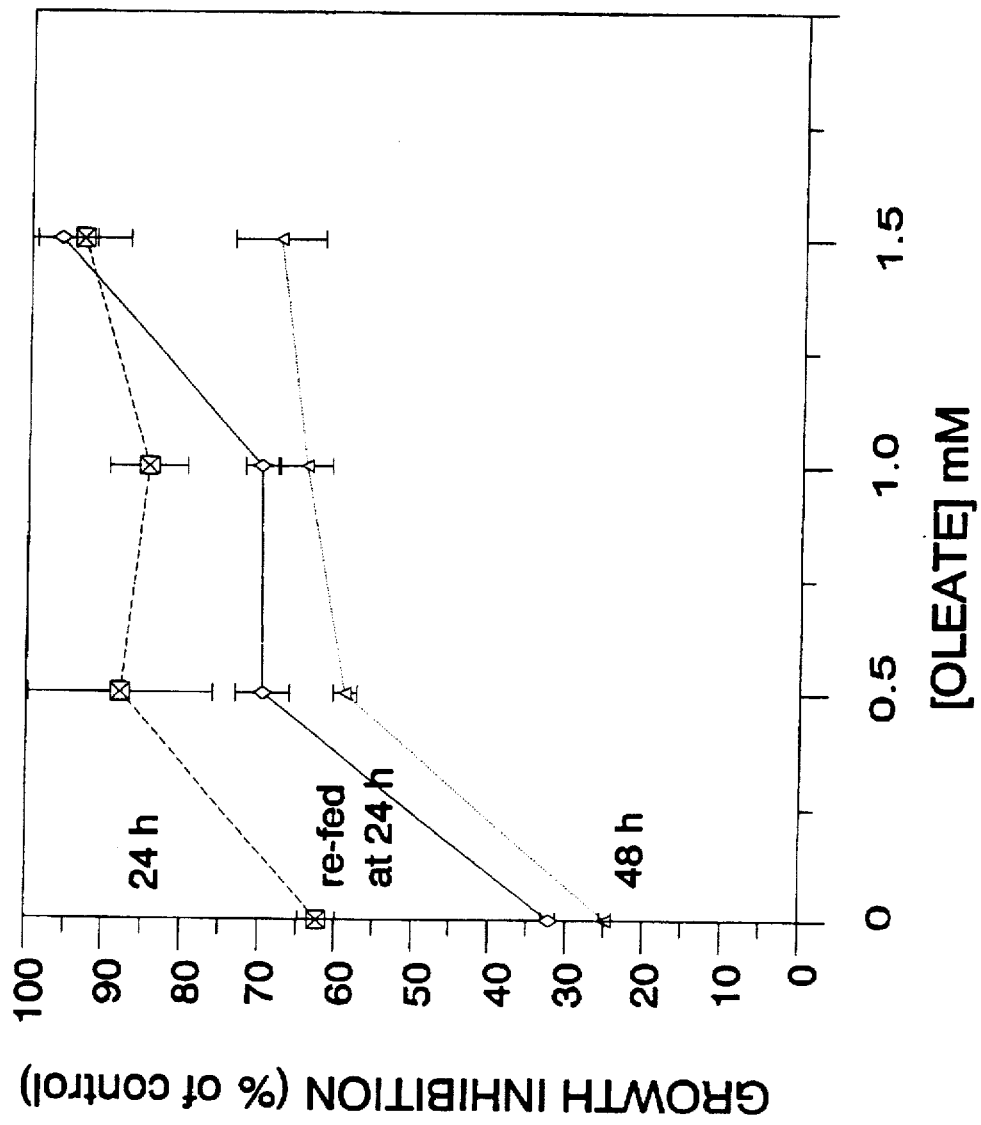
Figure 17: RESCUE OF HUMAN MAMMARY ZR-75-1 CELLS FROM CERULENIN GROWTH INHIBITION BY EXOGENOUS OLEATE

CHEMOTHERAPY FOR CANCER BY INHIBITING THE FATTY ACID BIOSYNTHETIC PATHWAY

This application is a Continuation-In-Part of U.S. Ser. No. 08/096,908, filed Jul. 26, 1993, now abandoned, which is a Continuation-In-Part of U.S. Ser. No. 07/917,716, filed Jul. 24, 1992, now abandoned, which is a Continuation-In-Part of U.S. Ser. No. 07/735,522, filed Jul. 26, 1991, now abandoned, which is a Continuation-In-Part of U.S. Ser. No. 07/622,407, filed Dec. 4, 1990, now abandoned, which is in turn a Continuation of U.S. Ser. No. 07/297,722, filed Jan. 17, 1989, now abandoned, which are incorporated herein in their entirety by reference.

The work leading to this invention was supported in part by Grant No. RO1 CA 46143 from the National Institutes of Health. The U.S. Government retains certain rights in this invention.

BACKGROUND OF THE INVENTION

1. Field of the Invention

This invention relates to the field of cancer chemotherapy. In particular, this invention contemplates administration to cancer patients of therapeutic agents which are cytotoxic or cytostatic to tumor cells.

2. Background Information

Some carcinoma cells are slow to grow, resulting in tumors that do not pose severe short term risk to a patient having such cells. For instance, many prostate cancers progress so slowly that they are only detected after the patient dies from another cause. Such carcinomas are safely left untreated. Other carcinomas metastasize and grow rapidly, resulting in death of the patient. Any treatment that can slow down the growth of these latter, more virulent carcinomas is desired.

Most current methods of cancer therapy include treatment with chemotherapeutic agents that inhibit cell division or radiation therapy that disrupts DNA in dividing cells. However, these treatments also affect normal cells that happen to be dividing or synthesizing DNA at the time of treatment. Therefore, there is a need for alternative treatments which are more specifically targeted to affect the cells of virulent tumors.

Fatty Acid Metabolism

The fatty acid biosynthetic pathway in man is comprised of four major enzymes: acetyl-CoA carboxylase, the rate limiting enzyme which synthesizes malonyl-CoA; malic enzyme, which produces NADPH; citrate lyase, which synthesizes acetyl-CoA; and fatty acid synthase, which catalyzes NADPH-dependent synthesis of fatty acids from acetyl-CoA and malonyl-CoA. The final products of fatty acid synthase are free fatty acids which require separate enzymatic derivatization with coenzyme-A for incorporation into other products. In man, significant fatty acid synthesis may occur in two sites: the liver, where palmitic acid is the predominant product (Roncari, *Can. J. Biochem.*, 52:221–230, 1974); and lactating mammary gland where $C_{10}$–$C_{14}$ fatty acids predominate (Thompson, et al., *Pediatr. Res.*, 19:139–143, 1985). Except for lactation, and cycling endometrium (Joyeux, et al., *J. Clip. Endocrinol. Metab.*, 70:1319–1324, 1990), the fatty acid biosynthetic pathway is of minor physiologic importance, since exogenous dietary fatty acid intake down-regulates the pathway in the liver and other organs (Weiss, et al., *Biol. Chest. Hoppe-Seyler*, 367:905–912, 1986).

In liver, acetyl-CoA carboxylase, malic enzyme and fatty acid synthase are induced in concert by thyroid hormone and insulin via transcriptional activation and repressed by glucagon (Goodridge, *Fed. Proc.*, 45:2399–2405, 1986) and fatty acid ingestion (Blake, et al., *J. Nutr.*, 120:1727–1729, 1990). Tumor necrosis factor alpha (TNF) a cytokine with profound effects on lipogenesis, is either stimulatory or inhibitory depending on the cell type studied. TNF markedly inhibits lipogenesis in adipocytes by reduction in acetyl-CoA carboxylase and fatty acid synthase protein synthesis, but is markedly stimulatory in the liver by increasing the level of citrate, which is the primary allosteric activator of the rate limiting enzyme of fatty acid biosynthesis, acetyl-CoA-carboxylase.

In lactating breast, the other major site of fatty acid biosynthesis in humans, fatty acid synthesis is under control of prolactin, estrogen, and progesterone. During pregnancy, progesterone acts as a mitogen to promote breast development and concomitantly down-regulates prolactin receptors, preventing lipid and milk protein synthesis before delivery. After delivery, the fall in estrogen and progesterone levels allows up-regulation of prolactin receptors and subsequent increase in lipogenic enzymes and milk protein production by breast epithelial cells.

Regulation of fatty acid synthase expression in human breast cancer has been studied primarily as a model for progesterone-stimulated gene expression. In contrast to normal lactating breast where progesterone stimulates epithelial cell growth while retarding lipogenic enzyme synthesis, in progesterone receptor (PR) positive human breast carcinomas such as MCF-7, ZR-75-1, and T-47D, progesterone inhibits growth and induces fatty acid synthase production along with other lipogenic enzymes (Chambon, et al., *J. Steroid Biochem.*, 33:915–922 (1989). Progesterone presumably acts to up-regulate fatty acid synthase expression via the steroid hormone response element as is found in the rat fatty acid synthase promoter (Amy, et al., *Biochem. J.*, 271:675–686, 1989), leading to increased FAS mRNA transcription or, by other mechanisms, to increased message stability (Joyeux, et al., *Mol. Endrocinol.*, 4:681–686, 1989). Regarding PR-negative human breast cancer cells, a single study reports that fatty acid synthase accounts for about 25% of cytosolic protein in SKBR3 cells but no data regarding its biologic significance or regulation was available (Thompson, et al., *Biochim. Biophys. Acta*, 662:125–130, 1981).

With regard to cytokines and other lipogenic hormones, only scant data are available concerning human breast cancer. For example, TNF has been known to be markedly growth inhibitory to some breast cancer cultures. While TNF is a2,0 mildly growth inhibitory to primary rat hepatocyte cultures ($ID_{50}$=5000 units/ml), some human breast cancer cells such as MCF-7 are extremely growth inhibited ($ID_{50}$= 40 units/ml) (Chapekar, et al., *Exp. Cell. Res.*, 185:247–257, 1989). The effect of TNF on FAS expression or lipogenic activity in breast cancer cells, however, remains unknown. One study of fatty acid synthase expression in MCF-7 cells using Northern analysis, found that insulin and insulin growth factor-1 were only slightly stimulatory compared to 5–10 fold increases seen with progesterone, while $T_3$ had no effect (Chalbos, et al., *J. Steroid Biochem. Molecc Biol.*, 43:223–228, 1992). Overall, regulation of FAS in receptor positive breast cancer has been only cursorily examined, while receptor negative tumors have not been studied.

No association with poor clinical outcome was found for breast or for any other cancers in those few systems where fatty acid synthase expression was studied. In the only study purporting to associate FAS expression with prognosis, fatty acid synthase expression was studied by in situ hybridization in 27 breast cancers, finding an association between increased fatty acid synthase mRNA and a higher degree of morphologic differentiation, but without association with estrogen or progesterone receptor status (Chalbos, et al., *J. Natl. Cancer Inst.*, 82:602–606, 1990). It was deduced from these data that fatty acid synthase expression in breast carcinoma is associated with greater degree of morphologic differentiation and therefore presumably with less aggressive tumors. A second study of 87 cases by Northern blotting of fatty acid synthase mRNA found an association of fatty acid synthase expression and young age (premenopausal patients), but again no association with receptor status (Wysocki, et al., *Anticancer Res.*, 10:1549–1552, 1990). Neither study provided clinical follow-up of their patients; there were no data comparing FAS expression with either disease-free interval or patient survival. Without clinical outcome, no reliable conclusions can be drawn regarding FAS expression and tumor virulence.

These studies stand in contrast to a series of greater than 200 patients from several centers demonstrating a strong association between poor prognosis and expression of a protein of undetermined function (designated OA-519) through measurement of disease-free survival or overall survival (Kuhajda, *N. Engl. J. Med.*, 321:636–641, 1989; Shurbaji, et al., *Am. J. Clin. Pathol*, 96:238–242, 1991; Corrigan, et al., *Am. J. Clin. Pathol.*, 96:406, 1991; Cote, et al., *Lab. Invest.*, 66:13A, 1992; Ziegler, et al., *Am. J. Clin. Oncol.*, 14:101–110, 1991).

Nor has fatty acid metabolism been a target of study in cancer therapeutics. Fujii, et al. (1986, *Japan J. Exp. Med.*, 56:99–106), used the fatty acid synthase inhibitor cerulenin in combination with exogenous antitumor antibodies to weaken the cell membrane in an attempt to potentiate complement-mediated cell membrane damage via the membrane attack complex. Cerulenin was known to be toxic to cells at high concentration, and Fujii, et al., taught that the cerulenin concentration should be kept low to maintain the selectivity conferred by the humoral immune component of complement-mediated cell lysis. Spielvogel, et al., U.S. Pat. No. 5,143,907, noted that a series of phosphite-borane compounds exhibited both antineoplastic activity and anti-inflammatory activity while lowering serum cholesterol and serum triglycerides. The phosphite-borane compounds are non-specfic inhibitors that affect many cellular functions, and so they are not selectively effective against tumor cells. Spielvogel, et al. taught that the hypolipidemic effect on serum cholesterol and triglycerides was mediated through more than one mechanism, and the antineoplastic effect was not shown to be related to the hypolipidemic activity.

SUMMARY OF THE INVENTION

It is an object of this invention to provide a method for treating carcinoma in a mammal which will reduce the tumor burden of the mammal.

It is another object of this invention to provide a method for treating virulent carcinomas.

The present invention provides a method of treating mammals with carcinoma by inhibiting fatty acid synthesis by the cells of the carcinoma, such that growth of the cells is inhibited in a manner selectively cytotoxic or cytostatic to the cancer cells.

In a more particular embodiment, the invention provides a method of treating mammals with carcinoma by administering fatty acid synthase (FAS) inhibitors or inhibitors of other enzymes of the synthetic pathway for fatty acid as cytotoxic chemotherapeutic agents, thereby reducing tumor burden.

In a further embodiment, the present invention provides a method of ameliorating tumor burden in a carcinoma patient having tumor tissue which expresses a protein that exhibits fatty acid synthase activity, comprising administering a therapeutically effective amount of a fatty acid synthase inhibitor to the patient. Expression may be determined directly in tumor tissues by detecting fatty acid synthase in tissue samples obtained from procedures such as biopsies, resections or needle aspirates, using assays such as immunohistochemistry, cytosol enzyme immunoassay or radioimmunoassay, or direct measurement of enzyme activity. Expression of fatty acid synthase by the tumor may be indirectly measured by detecting fatty acid synthase in plasma or body fluid using assays such as enzyme immunoassay or radioimmunoassay.

In a further embodiment, the invention provides a method for treating mammals with carcinoma while protecting normal (non-neoplastic) tissues (such as liver, which may normally express fatty acid synthase activity) over a wide range from potential toxicity, by down-regulating the FAS enzyme activity of normal cells before and/or during administration of therapeutically effective amounts of FAS inhibitors. Down regulation may be accomplished by, for instance, reduction of caloric intake or other effective methods.

The present inventors have discovered the prognostic significance of a protein (designated as OA-519) which is expressed in breast cancers and other carcinomas. Particularly virulent carcinomas tend, among other things, to have cells that express OA-519, and this particular protein has been found to have fatty acid synthase activity which appears to be a required enzyme activity for the growth of carcinomas but not necessarily for normal cells. The inventors have further discovered that inhibitors of fatty acid synthase (FAS inhibitors) are cytotoxic to cells that express OA-519. Based on these discoveries, the inventors have developed the present method of treating carcinoma patients by administering inhibitors of fatty acid synthesis to reduce tumor burden in the patients. The method of the present invention is particularly advantageous because treatment with inhibitors such as FAS inhibitors is selective for cells expressing fatty acid synthase. FAS is an inducible enzyme that is not generally expressed by normal cells, and as a result, the tumor cells are preferentially affected by the inhibitors.

BRIEF DESCRIPTION OF THE FIGURES

The file of the patent contains at least one drawing executed in color. Copies of this patent with color drawings will be provided by the Patent and Trademark Office upon request and payment of the necessary fee.

FIG. 1A shows the prognostic correlation between expression of OA-519 and progesterone receptor (PR) in breast cancer.

FIG. 2A shows the correlation between OA-519 expression and disease free survival in prostate cancer.

FIG. 3A shows the 34-amino acid sequence of a peptide immunologically cross-reactive with OA-519. The sequence corresponds to the first 34 amino acids encoded by the hpr gene reported by Maeda, J. Biol. Chem., vol. 260, pp. 6698–6709, 1985.

FIG. 3B shows Peptide Sequence Analysis of OA-519.

FIG. 11A and B show the relative growth inhibition of cerulenin to different mammary carcinoma cell lines.

FIG. 12A and B demonstrate that cerulenin concentration correlates with inhibition of acyl-glyceride synthesis but not with inhibition of cholesterol synthesis.

FIG. 13 shows lack of correlation between cell proliferation rate and susceptibility to cerulenin inhibition.

FIG. 14 shows growth inhibition of cerulenin to prostatic carcinoma lines.

FIG. 15 shows selective growth inhibition by TOFA of selective mammary carcinoma lines with higher levels of endogenous fatty acid biosynthesis.

FIG. 16 shows the growth inhibitory effects of Triacsin-C and cerulenin on tumor cells expressing OA-519$_{FAS}$.

FIG. 17 shows that exogenously added fatty acids can overcome the inhibition of FAS and rescue cells from the growth inhibitory effect of cerulenin.

DETAILED DESCRIPTION OF THE EMBODIMENTS

Figure 1:
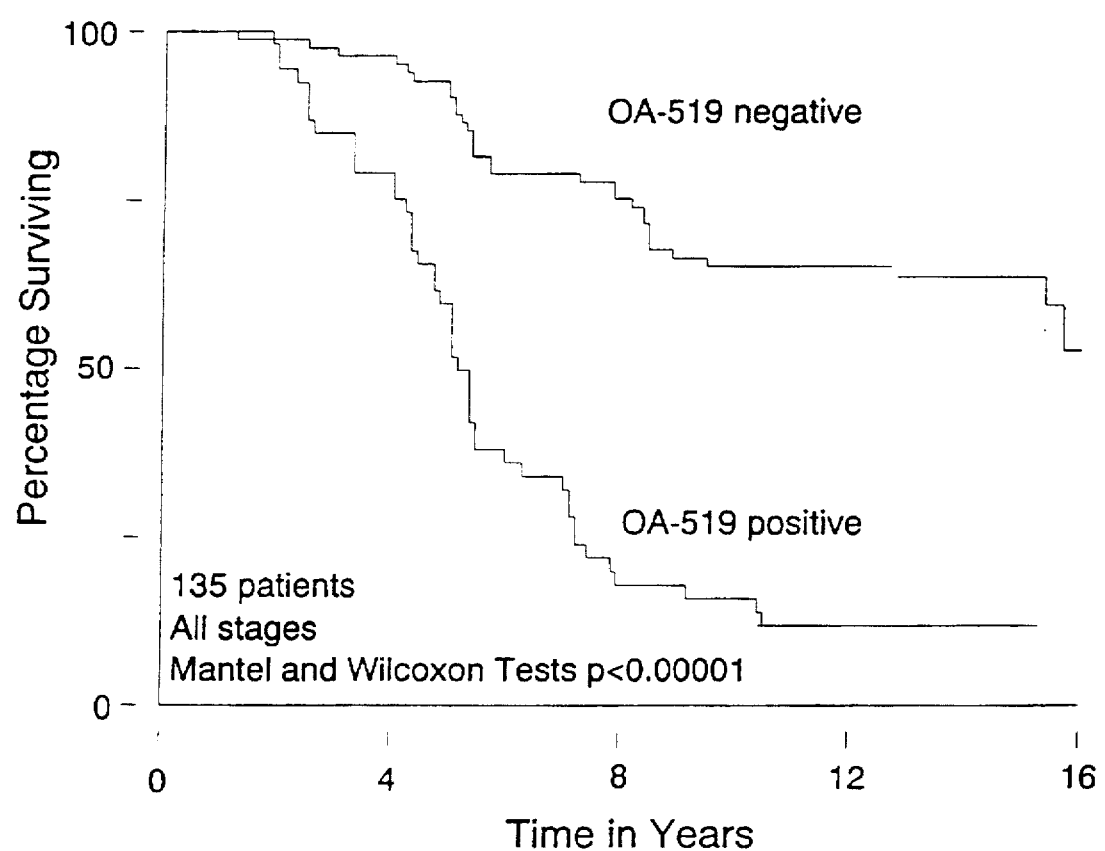
FIG. 1 shows the correlation between OA-519 Expression and Survival in Breast Carcinoma.

I. Discovery of a New, Tumor-related Enzyme Activity

The present inventors have discovered a protein which is specifically immunoreactive with antibodies specific for an epitope found on the peptide shown in FIG. 3A, but not on haptoglobin 1 or haptoglobin 2, and they have discovered that the protein is highly correlated with the most virulent carcinomas. This protein antigen has been designated OA-519 also referred to herein as OA-519$_{FAS}$. Studies on the survival of patients having a wide variety of carcinomas have demonstrated that detection of OA-519 in the tumor or the plasma of the patient correlates with poor prognosis to high statistical significance. (See Table 1.)

TABLE 1

OA-519 Expression and Cancer Prognosis
(as Determined by Immunohistochemistry)

| Tumor Type | Population | Prognostic Association | Reference |
|---|---|---|---|
| Breast | 70 (stages 1 & 2) | Disease recurrence 3.92 relative risk | A |
|  | 135 (all stages) | Survival, 4.86 relative risk | Martin, et al* |
|  | 49 (stages 1 & 2) | Early (<2 yr) recurrence | B |

TABLE 1-continued

OA-519 Expression and Cancer Prognosis
(as Determined by Immunohistochemistry)

| Tumor Type | Population | Prognostic Association | Reference |
|---|---|---|---|
|  |  | combined with progesterone receptor (p < 0.02) |  |
| Prostate | 42 (all stages) | Tumor grade (p < 0.006), tumor volume (p < 0.004) | C |
| Colon | 27 (all stages) | Distant metastases (p < 0.02) | D |
| Ovary | 34 (all stages) | Disease recurrence and survival (p < 0.05) | Kacinski, et al* |

A. Kuhajda, et al, N. Engl. J. Med., 321:636–41, 1989.
B. Cote, et al, Mod. Pathol., 5:13A, 1992.
C. Shurbaji, et al, Am. J. Clin. Pathol., 97:686–691, 1992.
D. Redston, et al, Mod. Pathol., 5:47A, 1992.
*See Example 1.

The inventors have isolated OA-519 and determined that the isolated protein exhibits fatty acid synthase activity. OA-519 purified from a human breast carcinoma cell line has peptide sequence homology with rat fatty acid synthase, and OA-519 also has functional characteristics of a fatty acid synthase. Fatty acid synthesis by OA-519 was demonstrated by incorporation of $^{14}$C malonyl coenzyme A into fatty acids, subsequent esterification of the fatty acids, and analysis by reversed-phase thin layer chromatography The specific activity of purified OA-519 was determined spectrophotometrically by following the oxidation of NADPH at 340 nm in the presence of acetyl coenzyme A and malonyl coenzyme A. In one determination, the specific activity of OA-519 was measured as 586 nanomoles NADPH oxidized/min/mg protein, which compares favorably with the value of 404 obtained for FAS from human liver.

Fatty acid synthase is a large protein found in the cytosol of cells from particular tissues, including liver and lactating mammary gland, but FAS is not expressed in most normal (non-malignant) adult tissues. Fatty acid synthase in higher organisms is a multifunctional enzyme which is well known to carry out the following seven enzymatic functions on, a single molecule (Wakil, S. J., Biochemistry, 28:4523–4530, 1989):

acetyl transacylase
malonyl transacylase
beta-ketoacyl synthetase (condensing enzyme)
beta-ketoacyl reductase
beta-hydroxyacyl dehydrase
enoyl reductase
thioesterase Breast cancer cells have been found to express fatty acid synthase, while most other tumor cells have not been tested for the presence or absence of this enzyme. Rochefort and co-workers have partially cloned FAS from breast cancer cells and found that FAS expression by breast cancer cell lines was correlated with responsiveness to progesterone (Chalbos, et al, J. Biol. Chem., 262:9923–9926, 1987). Based on this evidence, they concluded that cells expressing FAS were from tumors that were less de-differentiated and therefore less virulent (Chalbos, et al, J. Nat'l. Cancer Inst., 82:602–606, 1990). The present inventors have discovered that, contrary to the teaching of Rochefort, presence of OA-519, a protein which exhibits FAS activity, is highly correlated with the most virulent carcinomas.

Using standard in vitro growth inhibition assays, the inventors have demonstrated that inhibitors of OA-519 inhibit growth of carcinoma cells, but have little effect on normal human fibroblasts. Indeed, fibroblasts, which have very low FAS activity, are resistant to FAS inhibitor concentrations that inhibit growth of more than 80% of breast carcinoma cells having high levels of OA-519 activity. Studies with multiple breast, prostate, lung, colon, and ovarian carcinoma cell lines, and normal fibroblasts confirm the correlation between OA-519 synthase activity and growth inhibition by FAS inhibitors. The relationship between drug sensitivity and OA-519 enzyme activity holds for all tumor cell types tested. Thus, inhibition of the fatty acid synthase enzyme, which is highly expressed in the most virulent carcinomas, can inhibit the growth of cells in these tumors.

II. Treatment Based on Inhibition of Fatty Acid Synthesis

The present invention provides a method for ameliorating tumor burden in mammals having a carcinoma tumor which contains cells that are dependent on endogenously synthesized fatty acid (fatty acid synthesized within the cells). Such cells usually over-express a protein with FAS activity. Tumor burden may be reduced in such mammals by administering to the mammal one or more inhibitors that interfere with fatty acid synthesis or utilization. These inhibitors are cytotoxic to tumor cells which express FAS, and administration which results in reduction of fatty acid synthesis and utilization by the tissue and/or reduction of FAS activity in biological fluids of these mammals will reduce tumor burden.

A. Selection of the Patient Population

The method of this invention may be used to treat mammals suffering from cancers which have an elevated level of fatty acid synthase. Characteristic carcinomas amenable to treatment include those of bladder, salivary gland, skin adnexae, bile duct, endocervix, ectocervix, and vagina, esophagus, nasopharynx and oropharynx, or those of germ cell origin, and mesothelioma. In particular, carcinomas or adenocarcinomas of the stomach, endometrium, kidney, liver and lung, as well as melanoma are treatable according to this invention. Breast, colon and rectum, prostate, and ovary, are especially suitable types of adenocarcinomas for the application of this therapy.

The method of this invention contemplates treatment of tumors having cells that express FAS or depend on endogenous fatty acid (synthesized within the cell). Endogenous fatty acid synthesis by such cells will preferably occur at a rate of incorporation greater than 10 fmoles of acetyl-CoA into acyl glyceride per 200,000 cells per minute. Preferred patients may be identified because they have tumors containing cells which express OA-519 or other enzymes of the fatty acid synthesis pathway, such as acetyl CoA carboxylase (ACC), at levels higher than the level found in the surrounding normal (e.g., non-neoplastic) tissue. Such cells are aggressive tumor cells and result in decreased survival, increased metastasis, increased rates of clinical recurrence and overall worsened prognosis.

Tumor cell sensitivity to fatty acid synthesis inhibitors usually varies continuously with FAS levels. Aggressive tumor cells expressing levels of FAS activity greater than 20 femtomoles malonyl CoA incorporated into fatty acid per 200,000 cells per minute may be expected to be sensitive to fatty acid synthase inhibitors. Since many tumor cells are extremely dependent on endogenous fatty acid synthesis, lower FAS activity levels need not exclude a specific tumor as a candidate for therapy with fatty acid synthase inhibitors.

The presence of FAS in cells of the carcinoma may be detected by any suitable method, including activity assays or stains, immunoassays using anti-FAS antibodies, assays measuring FAS mRNA, and the like. Particularly preferred are assays for the presence of OA-519, a protein which is immunologically cross-reactive with the gene product of the hpr gene (Maeda, *J. Biol. Chem.*, vol. 260, pp. 6698–6709, 1985) but not with haptoglobin 1 or 2. Such assays are taught in International Patent Publication WO 90/08324 or U.S. application Ser. No. 07/735,522, incorporated herein by reference, or in the Examples, below. The most preferred assays are immunoassays for OA-519, either in tissue or in plasma.

Expression of FAS may be determined directly in tumor tissue samples obtained through procedures such as biopsies, resections or needle aspirates, using assays such as immunohistochemistry, cytosol enzyme immunoassay or radioimmunoassay, in situ hybridization of nucleic acid probes with mRNA targets having FAS sequences, or direct measurement of enzyme activity. Expression of fatty acid synthase by the tumor may be indirectly measured in biological fluid samples obtained from patients, such as blood, urine, serum, lymph, saliva, semen, ascites, or especially plasma, using any suitable assays. Preferred assays for FAS in biological fluid include enzyme immunoassay or radioimmunoassay.

Cells which depend on endogenously synthesized fatty acids may also be identified by detection of other enzymes of the fatty acid synthesis pathway at levels higher than those found in non-neoplastic tissue surrounding the tumor. In particular, treatment of cells having unexpectedly high levels of acetyl CoA carboxylase is contemplated by the present invention. The presence of these enzymes may be detected by assay methods analogous to those described for FAS.

Cells that require endogenously synthesized fatty acid are widespread among carcinomas, particularly the most virulent carcinomas. While it is preferred that the presence of FAS be determined prior to treatment, the skilled clinician will recognize that such determination is not always necessary. Treatment of a carcinoma patient with an inhibitor of fatty acid synthesis, particularly a FAS inhibitor, which results in reduction of tumor burden demonstrates the presence of FAS in the tumor. Where a carcinoma patient can be successfully treated by the method of this invention, independent determination of FAS may be unnecessary. Such empirical treatment of carcinomas of the type usually found to express FAS is also within the contemplation of this invention.

Fatty acid synthesis inhibitors are also useful in conjunction with other chemotherapeutic agents. Since no presently prescribed cancer chemotherapeutic agents are specifically active against the fatty acid synthase pathway, FAS inhibitors will complement existing anti-cancer drugs, particularly antimetabolic drugs that target other anabolic or catabolic pathways.

FAS expression and the growth inhibitory effect of inhibitors of the fatty acid synthetic pathway are independent of the cell cycle. Therefore, inhibitors of fatty acid synthesis may be expected to be particularly effective in combination with chemotherapeutic agents that target rapidly cycling cells. Alternatively, fatty acid synthesis inhibitors may be administered to supplement a chemotherapeutic regime based on antineoplastic agents known to be effective against the particular tumor type being treated. In particular, use of fatty acid synthesis inhibitors to prevent the growth of a small proportion of undetected but highly virulent cells in conjunction with a therapeutic program using other agents is within the contemplation of this invention.

On the other hand, it is not contemplated that fatty acid synthesis inhibitors will be useful in combination with agents which produce complement-mediated cell damage via the membrane attack complex, whether initiated by antibody or by the alternative pathway for complement activation (Bhakdi, et al. (1983), "Membrane Damage by Complement," *Biochim. Biophys. Acta*, 737:343:372). Therefore, this invention is not directed to the use of fatty acid synthesis inhibitors in the presence of exogenously supplied agents which activate the complement-dependent membrane attack complex.

B. Inhibition of the Fatty Acid Synthetic Pathway

Carcinoma cells which are dependent on their own endogenously synthesized fatty acid will express FAS. This is shown both by the fact that FAS inhibitors are growth inhibitory and by the fact that exogenously added fatty acids can protect normal cells but not these carcinoma cells from FAS inhibitors. Therefore, preventing synthesis of fatty acids by the cell may be used to treat carcinoma.

Fatty acids are synthesized by fatty acid synthase (FAS) using the substrates acetyl CoA, malonyl CoA and NADPH. Thus, the fatty acid synthesis pathway is usually considered to involve four enzymes—FAS and the three enzymes which produce its substrates: acetyl CoA carboxylase (ACC), malic enzyme and citrate lyase. Other enzymes which can feed substrates into the pathway, such as the enzymes which produce NADPH via the hexose monophosphate shunt, may also affect the rate of fatty acid synthesis, and thus be important in cells that depend on endogenously synthesized fatty acid. Inhibition of the expression or the activity of any of these enzymes will affect growth of carcinoma cells that are dependent on endogenously synthesized fatty acid. In accordance with this invention, any suitable method for inhibiting fatty acid synthesis by carcinoma cells may be used to reduce tumor burden in carcinoma patients, including especially inhibitors of the activities of any of the four enzymes of the pathway The product of FAS is a free $C_{12}$–$C_{16}$ fatty acid, usually palmitate. Palmitic acid must be further processed to fulfill the cell's need for various lipid components. As used herein, the term "lipid biosynthesis" refers to any one or a combination of steps that occur in the synthesis of fatty acids or subsequent processing of fatty acids to make cellular components containing fatty acids. The first step in this downstream processing is activation of the fatty acid by coupling it to coenzyme A, which is catalyzed by an enzyme, acyl CoA synthetase.

Inhibition of key steps in down-stream processing or utilization of fatty acids may be expected to inhibit cell function, whether the cell depends on endogenous fatty acid or utilizes fatty acid supplied from outside the cell, and so inhibitors of these down-stream steps may not be sufficiently selective for tumor cells that depend on endogenous fatty acid. However, it has been discovered that administration of a fatty acid synthesis inhibitor to such cells makes them more sensitive to inhibition by inhibitors of down-stream fatty acid processing and/or utilization. Because of this synergy, administration of a fatty acid synthesis inhibitor in combination with one or more inhibitors of down-stream steps in lipid biosynthesis and/or utilization will selectively affect tumor cells that depend on endogenously synthesized fatty acid. Preferred combinations include an inhibitor of acyl CoA synthetase combined with an inhibitor of FAS or ACC.

C. Inhibitors of Fatty Acid Synthesis

When it has been determined that a mammal has a tumor which expresses FAS, or if OA-519 has been found in a biological fluid from a cancer patient, the mammal or patient may be treated according to the method of this invention by administering a fatty acid synthesis inhibitor to the patient. Inhibitors whose administration is within the contemplation of this invention may include any compound that shows demonstrable inhibition of lipid biosynthesis or utilization by a cell. Preferred fatty acid synthesis inhibitors are listed in U.S. patent application Ser. No. 08/188,409 entitled "Novel Compounds for Fatty Acid Synthesis Inhibition," filed on even date with this application and incorporated herein by reference.

Any compound that inhibits fatty acid synthesis may be used to inhibit tumor cell growth, but of course, compounds administered to a patient must not be equally toxic to both malignant and normal (non-malignant) cells. Preferred inhibitors for use in the method of this invention are those with high therapeutic indices (therapeutic index is the ratio of the concentration which affects normal cells to the concentration which affects tumor cells). Inhibitors with high therapeutic index can be identified by comparing the effect of the inhibitor on two cell lines, one non-malignant line, such as a normal fibroblast line, and one carcinoma line which has been shown to express high levels of OA-519. In particular, therapeutic index may be determined by comparing growth inhibition of animal cells such as human cell lines exhibiting a low level of fatty acid synthesis activity, preferably less than about 10 fmole acetyl-CoA incorporation into acyl glyceride per minute per 200,000, cells, to growth inhibition of human cancer cells exhibiting a high level of fatty acid synthetic activity, preferably greater than about 20 fmole acetyl-CoA incorporation per 200,000 cells per minute, more preferably at least about 80 fmole acetyl-CoA incorporation into acyl glyceride per 200,000 cells per minute. Cells with the preferred level of fatty acid synthesis activity are easily obtained by the skilled worker, and examples of publicly available cell lines are provided in Example 7 below. Preferably, the growth inhibition assays are performed in the presence of exogenous fatty acid added to the cell culture medium, for example, 0.5 mM linoleic acid.

Inhibitors can be characterized by the concentration required to inhibit cell growth by 50% ($IC_{50}$ or $ID_{50}$). FAS inhibitors with high therapeutic index will, for example, be growth inhibitory to the carcinoma cells at a lower concentration (as measured by $IC_{50}$) than the $IC_{50}$ for the non-malignant cells. Inhibitors whose effects on these two cell types show greater differences are more preferred. Preferred inhibitors of fatty acid synthesis will have $IC_{50}$ for cells with high fatty acid synthetic activity that is at least ½ log lower, more preferably at least 1 log lower, than the inhibitor's $IC_{50}$ determined for cells with low activity.

When tumors are treated by administration of a synergistic combination of at least one inhibitor of fatty acid synthesis and at least one inhibitor of either the enzymes which supply substrates to the fatty acid synthesis pathway or the enzymes that catalyze downstream processing and/or utilization of fatty acids, the therapeutic index will be sensitive to the concentrations of the component inhibitors of the combination. Optimization of the concentrations of the individual components by comparison of the effects of particular mixtures on non-malignant and OA-519-expressing cells is a routine matter for the skilled artisan. The dose of individual components needed to achieve the therapeutic effect can then be determined by standard pharmaceutical methods, taking into account the pharmacology of the individual components.

The inhibitor of fatty acid synthesis, or the synergistic combination of inhibitors will be administered at a level (based on dose and duration of therapy) below the level that would kill the animal being treated. Preferably, administration will be at a level that will not irreversibly injure vital organs, or will not lead to a permanent reduction in liver function, kidney function, cardiopulmonary function, gastrointestinal function, genitourinary function, integumentary function, musculoskeletal function, or neurologic function. On the other hand, administration of inhibitors at a level that kills some cells which will subsequently be regenerated (e.g., endometrial cells) is not necessarily excluded.

Acetyl CoA carboxylase and the condensing enzyme of the FAS complex are likely candidates for inhibition. Fatty acid synthesis would be reduced or stopped by inhibitors of these enzymes. The result would be deprivation of membrane lipids, which would cause cell death. Normal cells, however, would survive as they are able to import circulating lipid. Acetyl CoA carboxylase is the focal point for control of lipid biosynthesis. The condensing enzyme of the FAS complex is well characterized in terms of structure and function; the active center contains a critical cysteine thiol, which is the target of antilipidemic reagents, such as cerulenin.

A wide variety of compounds have been shown to inhibit fatty acid synthase (FAS), and selection of a suitable FAS inhibitor for treatment of carcinoma patients is within the skill of the ordinary worker in this art. FAS inhibitors can be identified by testing the ability of a compound to inhibit fatty acid synthase activity using purified enzyme. Fatty acid synthase activity can be measured spectrophotometrically based on the oxidation of NADPH, or radioactively by measuring the incorporation of radiolabeled acetyl- or malonyl-CoA. (Dils, et al, Methods Enzymol, 35:74–83). Suitable FAS inhibitors may be selected, for example, from those exemplified in Table 2.

Table 2

Representative Inhibitors Of The Enzymes Of The Fatty Acid Synthesis Pathway
Inhibitors of Fatty Acid Synthase
  1,3-dibromopropanone
  Ellman's reagent [5,5'-dithiobis(2-nitrobenzoic acid), DTNB]
  4-(4'-chlorobenzyloxy) benzyl nicotinate (KCD-232)
  4-(4'-chlorobenzyloxy) benzoic acid (MII)
  2[5(4-chlorophenyl)pentyl]oxirane-2-carboxylate (POCA) and its CoA derivative
  ethoxyformic anhydride
  thiolactomycin
  cerulenin
  phenyocerulenin
  melarsoprol
  iodoacetate
  phenylarsineoxide
  pentostam
  melittin
  methyl malonyl CoA
Inhibitors for citrate lyase
  (−) hydroxycitrate
  (R,S)-S-(3,4-dicarboxy-3-hydroxy-3-methyl-butyl)-CoA
  S-carboxymethyl-CoA
Inhibitors for acetyl CoA carboxylase
  sethoxydim
  haloxyfop and its CoA ester
  diclofop and its CoA ester
  clethodim
  alloxydim
  trifop
  clofibric acid
  2,4-D mecoprop
  dalapon
  2-alkyl glutarate
  2-tetradecanylglutarate (TDG)
  2-octylglutaric acid
  9-decenyl-1-pentenedioic acid
  decanyl-2-pentenedioic acid
  decanyl-1-pentenedioic acid
  (S)-ibuprofenyl-CoA
  (R)-ibuprofenyl-CoA
  fluazifop and its CoA ester
  clofop
  5-(tetradecycloxy)-2-furoic acid
  beta, beta'-tetramethylhexadecanedioic acid
  tralkoxydim
  free or monothioester of beta, beta prime-methyl-substituted hexadecanedioic acid (MEDICA 16)
  alpha-cyanco-4-hydroxycinnamate
  S-(4-bromo-2,3-dioxobutyl)-CoA
  p-hydroxymercuribenzoate (PHMB)
  N6,02-dibutyryl adenosine cyclic 3',5'-monophosphate
  N6,02-dibutyryl adenosine cyclic 3',5'-monophosphate
  N2,02-dibutyryl guanosine cyclic 3',5'-monophosphate
  CoA derivative of 5-(tetradecyloxy)-2-furoic acid (TOFA)
  2,3,7,8-tetrachlorodibenzo-p-dioxin
Inhibitors for malic enzyme
  periodate-oxidized 3-aminopyridine adenine dinucleotide phosphate
  5,5'-dithiobis(2-nitrobenzoic acid)
  p-hydroxymercuribenzoate
  N-ethylmaleimide
  oxalyl thiol esters such as S-oxalylglutathione
  gossypol
  phenylglyoxal
  2,3-butanedione
  bromopyruvate
  pregnenolone The drug melarsoprol is a trivalent arsenical compound; Pentostam is a pentavalent antimony compound. Trivalent arsenicals react with adjacent thiol groups as do pentavalent antimonials. Fatty acid synthase activity requires multiple reduced thiol groups which would act as targets for inhibition by melarsoprol and other SH reagents.

Aside from these anti-parasite drugs, there are a host of other compounds which inhibit FAS at a variety of sites: protein kinase inhibitors block transcription; colchicine interference with microtubules blocks insulin induction of FAS; melittin, a peptide from bee venom cross-links to the acyl carrier protein of FAS from some species; and cerulenin, an antibiotic, blocks the condensing enzyme activity of FAS. Cerulenin is a specific inhibitor of the condensing enzyme activity of fatty acid synthase as demonstrated by Funabashi, et al (J. Biochem, 105:751–755, 1989) and cerulenin or phenylcerulenin are preferred FAS inhibitors for the method of this invention.

Preferred inhibitors of the condensing enzyme include a wide range of chemical compounds, including alkylating agents, oxididents, and reagents capable of undergoing disulphide interchange. The binding pocket of the enzyme prefers long chain, E, E, dienes such as:

In principal, a reagent containing the sidechain diene shown above and a group which exhibits reactivity with thiolate anions could be a good inhibitor of the condensing enzyme. Cerulenin (2S) (3R) 2,3-epoxy-4-oxo-7,10 dodecadienoyl amide is an example:

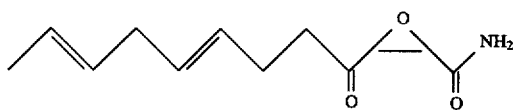

Examples of alternative compounds with different functional groups and the diene sidechain are shown below:

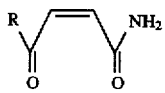

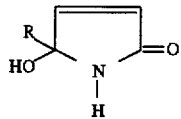

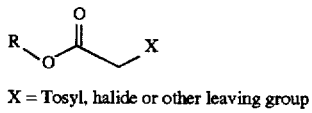

X = Tosyl, halide or other leaving group

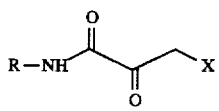

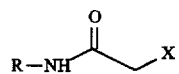

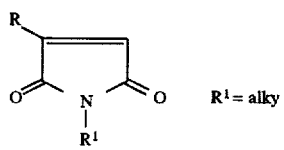

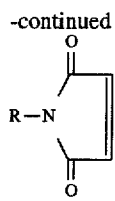

The R group tail can be varied according to the report of Morisaki, et. al. [*Eur. J. Biochem.* 211, 111 (1993)]. Increasing or decreasing the length of the sidechain reduces the inhibitory potency. Tetrahydrocerulenin is 80–150 times less potent than cerulenin. This result is consistent with the idea of $\pi$ electrons in the side chain being of importance in bonding. Also, the trans double bonds confer conformational rigidity which may also be important.

In an alternative embodiment of this invention, carcinoma patients are treated by administering compounds which inhibit either acetyl CoA carboxylase, malic enzyme or citrate lyase. Representative inhibitors of these enzymes are shown in Table 2. The considerations for selection of the particular inhibitor are the same as discussed above for FAS inhibitors.

Assays for acetyl-CoA carboxylase are taught in U.S. Pat. No. 5,143,907, incorporated herein by reference, and these assays can be used by the skilled worker to determine the inhibitory constants for ACC inhibitors by well-known procedures.

Propanoates which inhibit acetyl CoA carboxylases from diverse organisms are preferred inhibitors. The inhibitors may be represented by the general structure shown below:

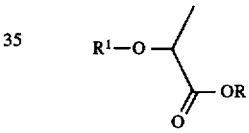

R can be hydrogen, alkyl, or aryl. The configuration at the asymmetric carbon atom can be R, S, or racemic. The acetyl CoA carboxylase in plants is often more susceptible to the R isomer. $R^1$ is often aryl-oxy-aryl:

Ar—O—Ar—

The aromatic rings can be benzene, pyridine, etc. Halo- and other substituents on the aromatic rings are permissible. Examples of propanoates are shown below and/or listed in the Table 2:

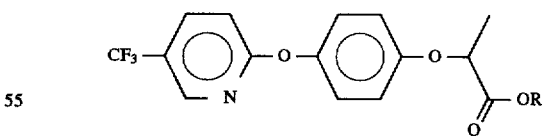

Fluazifop

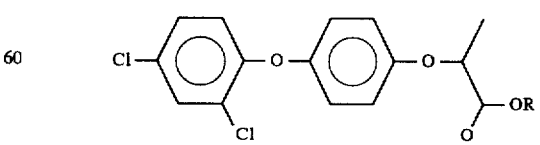

Diclofop

-continued

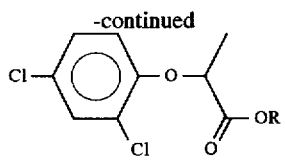

Dichlorprop

Dichlorprop

Some homologs of propanoates are good inhibitors. An example is TOFA, 5 (tetradecyloxy)-2-furoic acid, a potent acetyl CoA carboxylase inhibitor. The structure is shown below:

C-2 in this case is not chiral. The R group is a linear saturated 14-carbon sidechain. Methods of synthesizing this compound and related compounds that are also contemplated by this invention are taught in U.S. Pat. No. 4,146,623, incorporated herein by reference.

Another example of a homolog of the propanoates is TDGA or tetradecyglycidic acid:

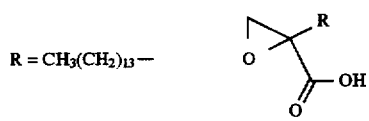

Hydrophobic character and a carboxyl carbon beta to an ether oxygen are common structural traits. Other relevant 2-substituted propanoates include compounds such as ibuprofen, ibuproxam and derivatives thereof.

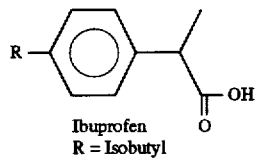

Ibuprofen
R = Isobutyl

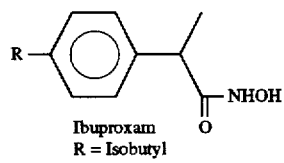

Ibuproxam
R = Isobutyl

Ketocylohexenes represent another class of acetyl CoA carboxylase inhibitors. One example is sethoxydim:

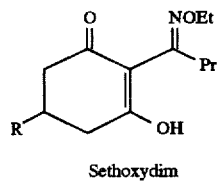

Sethoxydim

Where R is an ethylthiopropyl group.
Another class of compounds which inhibit acetyl CoA carboxylases is represented by the general structure:

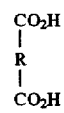

Specific examples such as glutaric acid and pentenedioic acids are listed in Table 2.

In addition to acetyl CoA carboxylase and FAS, other target enzymes include citrate lyase and malic enzyme. These enzymes provide acetate and NADPH for lipid biosynthesis via FAS. The respective reactions are as follows:

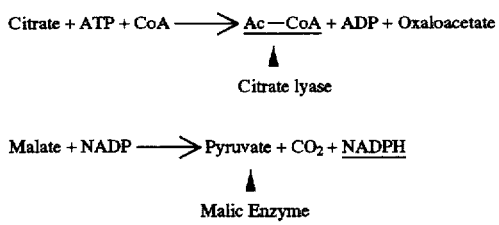

Therapeutic compounds could also be based on these inhibitors as the deprivation of acetyl CoA or NADH would also stop the lipid synthesis.

Of the enzymes in the fatty acid synthetic pathway, FAS is the preferred target for inhibition because it acts only within the pathway to fatty acids, while the other three enzymes are implicated in other cellular functions. Therefore, inhibition of one of the other three enzymes is more likely to affect normal cells. However, where an inhibitor for one of these enzymes can be shown to have a high therapeutic index as described above, the inhibitor may be used therapeutically according to this invention. The skilled clinician will be able to select a method of administration and to administer inhibitors of any enzyme in the synthetic pathway for fatty acids to treat carcinoma patients in need of such treatment, based on the teaching below.

This invention does not contemplate the use of inhibitors that are generally inhibitory to a large number of different cellular enzyme systems and pathways, such as the phosphite-boranes disclosed in U.S. Pat. No. 5,143,907, or iodoacetamide unless the particular inhibitor can be made relatively specific for lipid biosynthesis as shown by a high therapeutic index (for example, as part of a synergistic combination discussed above).

Palmitate is the major product of the fatty acid synthetase pathway. The elongation and oxidation of palmitate may be critical for production of necessary membrane lipids. For that purpose, the elongation and oxidation steps and any other processing steps for fatty acids would be likely molecular targets for therapeutics. To be incorporated into lipids, both endogenously synthesized fatty acids and exogenous dietary fatty acids must first be activated by acyl-CoA synthetase. Long-chain fatty acyl-CoA is an essential metabolite for animal cells, and so acyl-CoA synthetase is a preferred target.

Tomoda and colleagues (Tomoda et. al., Biochim. Biophys. Act 921:595–598 1987; Omura et. al., J. Antibiotics 39:1211–1218 1986) describe Triacsin C (sometimes termed WS-1228A), a naturally occurring acyl-CoA synthetase inhibitor, which is a product of Streptomyces sp. SK-1894. The chemical structure of Triacsin C is 1-hydroxy-3-(E, E, E-2', 4', 7'- undecatrienylidine) triazene. Triacsin C causes 50% inhibition of rat liver acyl-CoA synthetase at 8.7 µM; a related compound, Triacsin A, inhibits acyl CoA-synthetase by a mechanism which is competitive for long-chain fatty acids. Inhibition of acyl-CoA synthetase is toxic to animal cells. Tomoda et. al. (Tomoda et. al., J. Biol. Chem. 266:4214–4219, 1991) teaches that Triacsin C causes growth inhibition in Raji cells at 1.0 µM, and have also been shown to inhibit growth of Vero and Hela cells. Tomoda et. al. further teaches that acyl-CoA synthetase is essential in animal cells and that inhibition of the enzyme has lethal effects.

Lipid synthesis consists of multiple enzymatic steps. The data demonstrate that inhibition of lipid biosynthesis at two or more steps can create synergistic effects, lowering both the required concentration and the potential toxicity of any single agent. Since acyl-CoA synthetase is a ubiquitous enzyme apparently required by all cells for their continued well being, its inhibitors are potentially too toxic to be used effectively as a single anti-cancer agent. In contrast, when acyl-CoA synthetase inhibitors are paired with cerulenin, a specific fatty acid synthase inhibitor, synergistic effects are obtained, rendering each drug more effective.

D. Administration of Inhibitors of Fatty Acid Synthesis

Inhibitors of fatty acid synthesis are preferably formulated in pharmaceutical compositions containing the inhibitor and a pharmaceutically acceptable carrier. The pharmaceutical composition may contain other components so long as the other components do not reduce the effectiveness of the synthesis inhibitor so much that the therapy is negated. Pharmaceutically acceptable carriers are well known, and one skilled in the pharmaceutical art can easily select carriers suitable for particular routes of administration (*Remington's Pharmaceutical Sciences*, Mack Publishing Co., Easton, Pa., 1985).

The pharmaceutical compositions containing any of the inhibitors of this invention may be administered by parenteral (subcutaneously, intramuscularly, intravenously, intraperitoneally, intrapleurally, intravesicularly or intrathecally, topical, oral, rectal, or nasal route, as necessitated by choice of drug, tumor type, and tumor location.

Dose and duration of therapy will depend on a variety of factors, including the therapeutic index of the drugs, tumor type, patient age, patient weight, and tolerance of toxicity. Dose will generally be chosen to achieve serum concentrations from about 0.1 µg/ml to about 100 µg/ml. Preferably, initial dose levels will be selected based on their ability to achieve ambient concentrations shown to be effective in in-vitro models, such as that used to determine therapeutic index, and in-vivo models and in clinical trials, up to maximum tolerated levels. Standard procedure in oncology requires that chemotherapy be tailored to the individual patient and the circulatory concentration of the chemotherapeutic agent be monitored regularly. The dose of a particular drug and duration of therapy for a particular patient can be determined by the skilled clinician using standard pharmacological approaches in view of the above factors. The response to treatment may be monitored by analysis of blood or body fluid levels of fatty acid synthase, measurement of FAS activity or OA-519 levels in tumor tissue or monitoring tumor burden in the patient. The skilled clinician will adjust the dose and duration of therapy based on the response to treatment revealed by these measurements.

E. Selective Chemotherapeutic Method

In a preferred embodiment, the method of this invention also protects normal cells of patients treated with fatty acid synthesis inhibitors. To protect non-neoplastic normal tissues such as liver (which normally may express wide ranges of fatty acid synthase activity) from potential toxicity, the level of FAS enzyme and/or fatty acid synthetic activity may be down-regulated before and/or during therapy. Down regulation may be accomplished by supplying essential fatty acids in the diet, by reduction of caloric intake or by other effective methods, such as administration of glucagon.

Because FAS is an inducible enzyme in normal tissues, reduction in caloric intake will result in lower expression of FAS by normal cells. The most virulent tumor cells express FAS (OA-519) constitutively. In a patient with limited caloric intake, FAS expression is limited to tumor cells, and the cytotoxic effect of FAS inhibitors will be similarly limited. Down-regulation of FAS expression is usually coupled to fatty acid synthesis inhibitor therapy by reducing caloric intake of the patient before and during administration of the inhibitor.

Another suitable method of reducing FAS expression is exogenous administration of fatty acids, preferably, essential fatty acids. These fatty acids may be formulated in any way that results in the down-regulating FAS expression of normal cells. This could be by including them in the diet of the patient or by formulating them in the same pharmaceutical composition as the fatty acid synthesis inhibitor, or any other suitable method.

Diets suitable for reducing FAS expression in normal tissue are easily within the skill of the ordinary clinician. Any method of reducing FAS expression by normal cells is within the contemplation of the method of this invention, as long as the FAS level in normal cells is reduced during the time that the fatty acid synthesis inhibitor is present in the patient at levels that would be cytotoxic to tumor cells.

III. Non-invasive Therapy Using Inhibitors of Fatty Acid Synthesis

In a preferred mode, the inhibitor of fatty acid synthesis is formulated in a pharmaceutical composition and applied to an externally accessible surface of a patient having a neoplastic lesion in an externally accessible surface. Externally accessible surfaces include all surfaces that may be reached by non-invasive means (without cutting or puncturing the skin), including the skin surface itself, mucus membranes, such as those covering nasal, oral, gastrointestinal, or urogenital surfaces, and pulmonary surfaces, such as the alveolar sacs. Table 3 shows a list of neoplastic diseases that cause such lesions.

Table 3

Cancers Likely to Benefit from Topical Therapy
Directed at Endogenous Fatty Acid Synthesis
Basal Cell Carcinoma
Squamous Cell Carcinoma, including but not limited to these subtypes:
actinic keratosis
actinic cheilitis
cornu cutaneum
keratoacanthoma
squamous cell carcinoma in situ
dysplasia
Apocrine Carcinoma
Eccrine Carcinoma
Sebaceous Carcinoma
Merkel Cell Tumor
Paget's Disease (a cutaneous form of breast cancer)
Extramammary Paget's Disease
Cutaneous Melanoma
Transitional Cell Carcinoma
Other In situ or Dysplastic Lesions Neoplastic lesions in externally accessible surfaces are preferably treated by non-invasive administration of an inhibitor of fatty acid synthesis or by local invasive administration, such as intra-lesional injection, where the administration is substantially non-systemic. Administration of a pharmaceutical composition containing a fatty acid synthesis inhibitor is substantially non-systemic where biological effects of the inhibitor can be observed locally, but the systemic concentration of the inhibitor is below the level required for therapeutic effectiveness and also below the level at which the inhibitor would generate adverse side effects. Non-invasive administration includes (1) topical application to the skin in a formulation, such as an ointment or cream, which will retain the inhibitor in a localized area; (2) direct topical application to oropharyngeal tissues; (3) oral administration of non-absorbable agents or agents that are inactivated upon absorption; (4) nasal administration as an aerosol; (5) intravaginal application of the inhibitor formulated in a suppository, cream or foam; (6) direct application to the uterine cervix; (7) rectal administration via suppository, irrigation or other suitable means; (8) bladder irrigation; and (9) administration of aerosolized formulation of the inhibitor to the lung. Aerosolization may be accomplished by well known means, such as the means described in International Patent Publication WO 93/12756, pages 30–32, incorporated herein by reference.

While inhibitors of fatty acid synthesis formulated as described previously may be used for non-systemic administration, a preferred strategy is to administer these compounds locally or topically in gels, ointments, solutions, impregnated bandages, liposomes, or biodegradable microcapsules. Compositions or dosage forms for topical application may include solutions, lotions, ointments, creams, gels, suppositories, sprays, aerosols, suspensions, dusting powder, impregnated bandages and dressings, liposomes, biodegradable polymers, and artificial skin. Typical pharmaceutical carriers which make up the foregoing compositions include alginates, carboxymethylcellulose, methylcellulose, agarose, pectins, gelatins, collagen, vegetable oils, mineral oils, stearic acid, stearyl alcohol, petrolatum, polyethylene glycol, polysorbate, polylactate, polyglycolate, polyanhydrides, phospholipids, polyvinylpyrrolidone, and the like.

A particularly preferred formulation for fatty acid synthesis inhibitors is in liposomes. Liposomes containing fatty acid synthesis inhibitors according to this invention may be prepared by any of the methods known in the art for preparation of liposomes containing small molecule inclusions. Liposomes that are particularly suited for aerosol application to the lungs are described in International Patent Publication WO 93/12756, pages 25–29, incorporated herein by reference.

The concentrations of the active agent in pharmaceutically acceptable carriers may range from 1 pM to 100 mM. The dose used in a particular formulation or application will be determined by the requirements of the particular type of infection and the constraints imposed by the characteristics and capacities of the carrier materials. Dose and duration of therapy will depend on a variety of factors, including the therapeutic index of the drugs, type of infection, patient age, patient weight, and tolerance of toxicity. Preferably, initial dose levels will be selected based on their ability to achieve ambient concentrations shown to be effective against the target organism in-vitro, such as the model system used to determine therapeutic index, and in-vivo models and in clinical trials, up to is maximum tolerated levels. The dose of a particular drug and duration of therapy for a particular patient can be determined by the skilled clinician using standard pharmacological approaches in view of the above factors. The response to treatment may be monitored by analysis of blood or body fluid levels of fatty acid synthase, measurement of FAS activity or FAS levels in tissue or other standard monitoring techniques for determining the degree of sepsis in the patient. The skilled clinician will adjust the dose and duration of therapy based on the response to treatment revealed by these measurements.

The compositions described above may be combined or used together or in coordination with another antineoplastic substance.

EXAMPLES

The following Examples are provided for purposes of illustration only. They are not intended to limit the invention described above, which is only limited by the appended claims.

Example 1

OA-519 expression is associated with decreased survival in breast carcinoma and decreased survival and disease-free survival in prostate and ovarian carcinoma.

Example 7 of International Patent Publication WO 90/08324 or U.S. Ser. No. 07/735,522, incorporated herein by reference, demonstrated that OA-519 expression in breast carcinoma was associated with increased disease recurrence. Clinical studies confirm that OA-519 expression is associated with reduced overall survival in prostate and breast carcinoma and reduced overall and disease-free survival in ovarian carcinoma.

Breast Carcinoma

Patient Population: An inception cohort (patients entered into the study at the time of initial surgical treatment) of one hundred and thirty-five women with breast cancer were identified by the Norton Hospital tumor registry, all of whom were treated with mastectomy for primary infiltrating ductal breast carcinoma. The average patient age was 52 and ranged from 32 to 72 years. The average follow-up was 12.3 years and ranged from 10 to 16 years. Patients were admitted to the study when post-surgical treatment records, cause of death, survival time, and paraffin blocks of primary tumor were available for each patient. Estrogen and progesterone receptor information was determined immunohistochemically. In addition, patient age, dose and type of chemotherapy, radiotherapy, and hormonal therapy were documented. Type of infiltrating tumor and nuclear grade were also assessed using the criteria of Fisher et al (Fisher, et al, Cancer, 46:908–918, 1980).

Immunohistochemical Staining for OA-519: Immunohistochemical staining used monoclonal anti-OA-519 antibodies from hybridoma cells designated OA-519-M1 or HPR-2, which were deposited with the American Type Culture Collection, 12301 Parklawn Drive, Rockville, Md. 20852, on Jul. 26, 1991, under ATCC Accession No. HB 10853.

Briefly, the primary anti-OA-519 monoclonal antibody was incubated on the deparaffinized tissue sections at 2.5 ug/ml for 1 hour at 37° C. Following rinsing in rinse buffer, the slides were then incubated in 1/400 rabbit anti-mouse antibody (DAKO) for 1 hour. Following another rinse, the slides were incubated with avidin-linked horseradish peroxidase (Vectastaing ABC kit) for 1 hour. After the avidin-biotin complex formation, the slides were incubated in aqueous hematoxylin, coverslipped and observed.

OA-519 Immunoreactivity and Criteria for Positivity: Positive staining was finely granular, cytoplasmic, and heterogeneous. Additionally, staining either had to be visible at 100× magnification, or label at least 10% of tumor cells for a case to be scored positive.

Prognostic significance of OA-519 Immunoreactivity: Patients whose tumor-stained positively for OA-519 had a markedly increased risk of dying of breast carcinoma. FIG. 1 is a life table which shows the fate of OA-519 positive and negative patients. For example, after 12 years, about 37% of the OA-519 negative patients were dead compared to approximately 85% of the OA-519 positive patients.

The following table shows the significance of OA-519 reactivity by stage:

|  | STAGE 1 % dead | STAGE 2 % dead | STAGE 3 % dead |
| --- | --- | --- | --- |
| OA-519+ | 9/13 (70%) | 27/31 (87%) | 9/9 (100%) |
| OA-519− | 3/20 (15%) | 16/41 (39%) | 12/21 (57%) |
| p-value | 0.002 | <0.0001 | 0.019 |

Expression of OA-519 by Prostatic Adenocarcinoma

OA-519 expression in prostate cancer was also found to be associated with disease recurrence. Patients having been diagnosed and treated for prostate adenocarcinoma were selected from the files of the Mountain Home VA Medical Center. The study population included 99 patients with prostate cancer in American Urologic System (AUS) stages A through D1. Clinical Stage information was obtained from the tumor registry abstracts or by review of the clinical records. Patients were excluded from the study is they had distant metastasis at the time of presentation (AUS stage D2), their status at last follow up was unknown, or if the total follow up was less than two years.

Histopathologic Studies

Tumor grading: All slides were reviewed and a Gleason score was determined by adding the numbers for the two most predominant patterns (Gleason, in Tannenbaum M (ed): Urologic pathology: The prostate. Philadelphia, 1988, Lea & Febiger, pp. 171–198.). Gleason scores 2–4 were assigned Grade I, scores 5–7 were assigned grade II, and scores 8–10 were assigned Grade III.

Immunohistochemical Studies

A single representative tissue block was selected from each cancer for immunohistochemical staining. An affinity purified polyclonal antibody raised in rabbits against purified OA-519 was used in this study. Staining was performed on routinely processed, formalin fixed, paraffin embedded tissue. The Avidin—Biotin Complex (ABC) immunoperoxidase technique utilizing unlabeled primary antibody was used. In brief, 6 mm deparaffinized and rehydrated tissue sections were incubated in 5% nonfat dry milk in phosphate buffered saline (PBS) including 3% hydrogen peroxide for 20 minutes to block endogenous peroxidase activity as well as non-specific protein interactions. Slides were then incubated with affinity—purified polyclonal anti-OA-519 at 2.7 ug/ml in PBS at pH 7.2 for one hour at room temperature. With intervening washes with PBS, the sections were successively incubated with biotinylated goat anti-rabbit immunoglobulin diluted 1:200 in PBS (Vector Laboratories) and avidin-horseradish peroxidase complex (Vectastain$^R$, Vector Laboratories), both for 30 minutes at 22° C. Aminoethylcarbazole (AEC) (Vector Laboratories) was used as the chromogen with Mayer's hematoxylin counterstain. For negative controls, PBS was substituted for primary antibody for each case. A known anti-OA-519 positive case was used as a positive control with every run.

Staining was defined as positive for OA-519 epitopes if (1) immunoreactivity was discernible at lower power (100×) (2) granular cytoplasmic staining was present without observable nuclear staining, and (3) staining was heterogeneous (i.e., the level of reactivity varied from cell to cell or from region to region. Tumors were scored as positive or negative. Positive staining for OA-519 was seen in 56 (57%) of the 99 primary prostate cancers examined.

The mean total follow up time was 4.17 years (range, 2.01–9.33). Prostate cancer recurred or progressed in 19 (19%) of the patients. Progression was defined as the appearance of local or metastatic disease after "curative" treatment, such as radical prostatectomy or radiation, or advance in the stage of disease in patients treated with hormonal therapy or expectantly managed. The average time to progression of disease was 2.54 years (range 0.67–5.85).

Figure 2B:
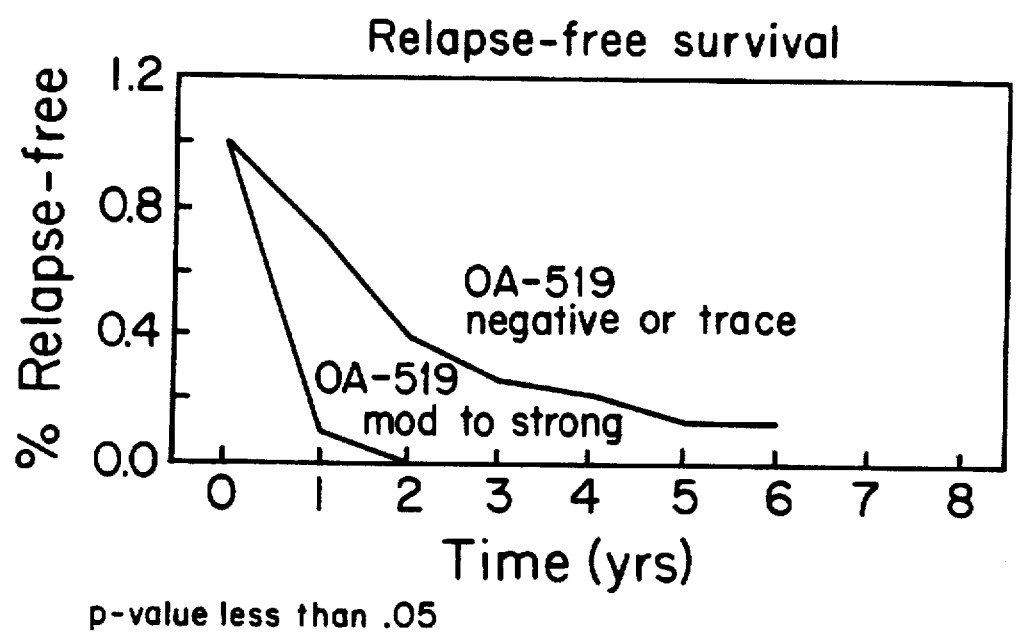
FIG. 2B(i) and FIG. 2B(ii) show shows the correlation between OA-519 Expression and Prognosis in Ovarian Carcinoma.

There were four (9%) cases of disease progression among the OA-519-negative group compared to 15 (27%) in the OA-519-positive group (Kaplan-Meier plot shown in FIG. 2A). The difference between these groups in the proportion of cancers that progressed was statistically significant (Wilcoxoni and log rank tests (P<0.009) and Fisher exact test (P<0.04)). OA-519 was a particularly valuable prognostic indicator among the low and intermediate grade prostate cancers, where the histologic grade by Gleason score was not a significant prognostic indicator (data not shown).

Ovarian Carcinoma

An ovarian carcinoma study by Kacinski et al. is in progress using the same antibody, staining procedure, and interpretation that was used in the above breast carcinoma study. However, based on analysis of 34 patients completed so far, there is an association of OA-519 expression with reduced disease-free and overall survival, which is demonstrated in FIG. 2B.

Example 1A

Prognostic Markers

OA-519 expression was strongly prognostic in early breast cancer, as shown in Example 1. This prognostic potential was independent of the prognostic power of estrogen and progesterone receptors. Increased expression of OA-519 in human breast carcinoma conferred a significantly worsened prognosis as measured either by disease recurrence or overall survival. In a clinical study of 135 patients with Stage I-III breast carcinoma (Martin, et al., manuscript in preparation), Cox multi-variate proportional hazard analysis demonstrated that OA-519 and progesterone receptor expression were most strongly and independently associated with adverse survival regardless of stage (univariate relative risk 4.860, 0.070; multi-variate relative risk 2.567, 0.153, respectively).

The prognostic power of OA-519 expression is further illustrated by the accompanying Kaplan-Meier plots (FIGS. 1 and 1A). FIG. 1 demonstrates that about 10% of OA-519 positive patients survived for 15 years as compared to about 50% of OA-519 negative patients. FIG. 1A graphically demonstrates the improved prognostic stratification when the two independent prognostic markers, OA-519 and progesterone receptor, are combined. This allowed stratification of patients into an OA-519 positive, progesterone receptor negative high risk group (88% dead), an OA-519 negative/progesterone receptor positive low risk group (5.4% dead), and an intermediate risk group (63% dead)

Among other markers included in this study, OA-519 was independent of p185$^{neu}$ and cathepsin D expression. Interestingly, OA-519 expression was not associated with tumor cell proliferation as measured by proliferating cell nuclear antigen. In a separate study of OA-5119 expression and S-phase determined by flow cytometry, OA-519 expression also showed no association with the S-phase fraction (Shurbaji. et al., Lab Pivest., 68:69A, 1993). Therefore, OA-519 expression could be utilized with the aforementioned, or any other independent prognostic marker to improve stratification of the patient population.

Example 2

Purification and Partial Sequence of OA-519 Piotein from Cell Lysates

OA-519 purified from a human breast carcinoma cell line has peptide sequence homology with rat fatty acid synthase, based on internal peptide sequence from OA-519, obtained by electroblotting a limited proteolytic digest of OA-519 with subsequent microsequencing directly from the PVDF membrane.

Figure 2C:
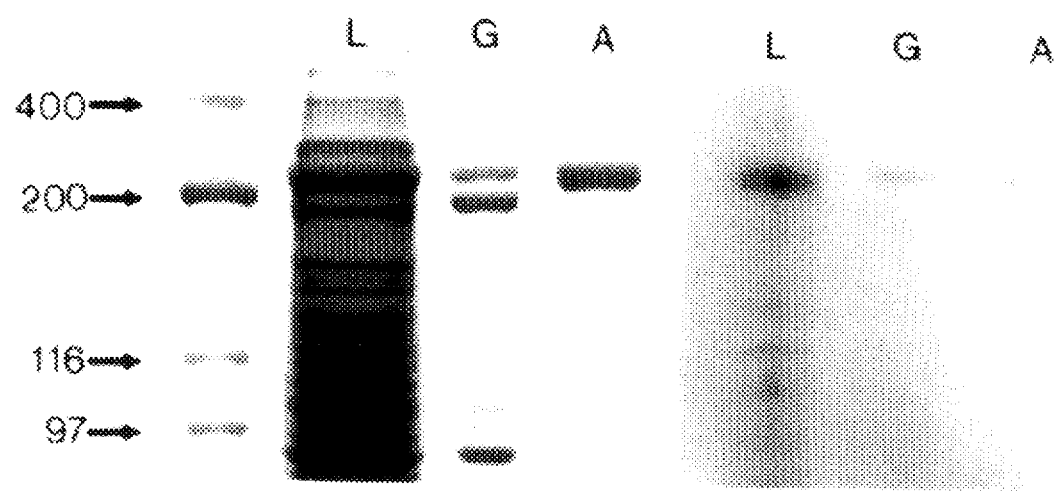
FIG. 2C shows the progressive purification of OA-519 from breast carcinoma by polyacrylamide gel electrophoresis and corresponding Western blots of proteins at various stages in the purification.

OA-519 was purified from the ZR-75-1 human breast carcinoma cell line, as demonstrated in FIG. 2C. The Figure shows 4–8% gradient gel SDS PAGE of a protein preparation in various stages of purification. The right hand panel is stained with Coomassie Blue, and the left hand panel is a Western blot using affinity purified polyclonal antibody raised against the peptide shown in FIG. 3A.

ZR-75-1 human breast carcinoma cells were grown to near confluence in medium. Confluent monolayers were rinsed with phosphate-buffered saline, then scraped free, harvested by centrifugation, and stored frozen.

To each aliquot of approximately $1.5 \times 10^7$ cells, 10 ml or purification buffer (20 mM Tris HCl, pH 7.5 at 4°, 1 mM EDTA, 0.1 mM diisopropylfluorophosphate, 0.1 mM phenylmethylsulfonyl fluoride) was added. Cells were homogenized with 10 strokes of a Dounce homogenizer, then clarified supernate was obtained by centrifugation at 16,000× g for 30 min. at 4° C. (Lane L of FIG. 2C was loaded with clarified ZR-75-1 hypotonic lysate.)

A Sephacryl S-200 (Pharmacia) gel filtration column, 2.5×90 cm, was pre-equilibrated with purification buffer, pH=8.0, containing 1 mM β-mercaptoethanol and 100 mM KCl. ZR-75 lysate was filtered through 0.45 mM filter, then loaded onto column at 25 ml/h. Fractions were analyzed for presence of 270,000 Da polypeptide by SDS-PAGB using a 4% Coomassie-stained gel. Presence of the polypeptide may optionally be confirmed by using Western blotting with either polyclonal antibody specific for peptide shown in FIG. 3A or anti-OA519 protein, developing the blots with $^{125}$I-protein A. (Lane G of FIG. 2C was loaded with pooled fractions from the gel filtration column.)

Positive fractions from the Sephacryl column were pooled, diluted with an equal volume of purification buffer plus 1 mM β-mercaptoethanol then loaded onto a pre-equilibrated Mono-Q HR 5/5 anion exchange HPLC column (Pharmacia). At a flow rate of 1 ml/min., the column was washed with 15 ml of purification buffer plus 1 mM P-mercaptoethanol, eluted with linear 60 ml gradient over 60 min. to a final 1M KCl concentration, then washed with 5 ml of 1M KCl-containing purification buffer plus 1 mM β-mercaptoethanol. Fractions containing the polypeptide were selected by SDS-PAGE using Coomassie-stained 4% gels. (Lane A in FIG. 2C was loaded with pooled fractions from the anion exchange column.) Fractions containing purified polypeptide, designated OA-519, were pooled and further processed according to downstream experimental needs. Characteristic yields were roughly 1 mg of OA-519 per $2 \times 10^7$ cells with purity of 98% or greater, estimated by Coomassie stained SDS polyacrylamide gels.

A final hydroxyapatite chromatography step was added to achieve more than 99% purity using a Bio-Rad MAPS Analytical HPHT Cartridge. Using a 0–600 millimolar phosphate gradient, OA-519 elutes in one peak at 200 millimolar phosphate.

Purified OA-519 was dialyzed into 50 millimolar ammonium bicarbonate, pH 8.0 and proteolytically cleaved with a 1:50 dilution of endoproteinase glutamate C (V8 protease) for 15 minutes at 37° C. The peptides were subjected to SDS-PAGE on 4% Laemmli gels and transferred to PVDF membranes (BioRad), and were sequenced directly from the PVDF membrane using automated Edman degradation on an Applied BioSystems gas phase sequencer (Matsudaira, P. T., "A Practical Guide To Protein and Peptide Purification for Micro-Sequencing", Academic Press, New York, 1989).

Limited proteolytic cleavage generated two major peptides of approximately 150 and 134 kD. The 150 kCD peptide had a blocked N-terminus and thus represented the N-terminal OA-519 peptide. N-terminal sequence was obtained from the 134 kD internal peptide which demonstrated 84.6% homology with rat fatty acid synthase over 13 amino acids as seen in FIG. 3B. Thus, OA-519 has structural homology with fatty acid synthase, also an approximately 270 kD molecule.

Example 3

OA-519 has Fatty Acid Synthase Activity

Purified OA-519 from the ZR-75-1 human breast carcinoma cell line has fatty acid synthase activity based on its ability to incorporate acetyl coenzyme A and malonyl coenzyme A into fatty acids in the presence of NADPH, a reaction specific for fatty acid synthase (Wakil, S. J., Biochemistry, 28:4523–4530, 1989). This reaction is specific for fatty acid synthase. Fatty acid synthesis by OA-519 was demonstrated by incorporation of $^{14}$C malonyl coenzyme A into fatty acids, subsequent esterification of the fatty acids, and analysis by reversed-phase thin layer chromatography.

Incorporation of $^{14}$C malonyl coenzyme A into fatty acids by OA-519: OA-519 was purified as in Example 2 except that protease inhibitors were omitted as they interfere with the final step of the synthase assay. 4.2 ug of OA-519 in 20 ul of 20 millimolar Tris HCl, 270 millimolar KCl, 1 millimolar EDTA, 1 millimolar DTT, pH 7.5 at 25° C. was added to the following reaction mixture: 75 nanomoles NADPH; 25 nanomoles acetyl coenzyme A; 16.6 ul of 1 molar potassium phosphate, pH 6.6 at 25° C.; and 97 ul HPLC grade water to a total volume of 150 ul. The reaction mixture was vortexed and 5 ul of $^{14}$C malonyl coenzyme A (20 uCi/ml; 51 mCi/millimolar) and 25 nanomoles malonyl coenzyme A were added. Following vortexing, the reaction mixture was incubated at 37° C. for 20 minutes and stopped by the addition of 1 ml of 1:1 chloroform:methanol.

Methyl esterification of $^{14}$C fatty acids: Prior to thin layer chromatographic separation of the $^{14}$C fatty acid mixture, methyl esters of the $^{14}$C fatty acids were prepared using the method of methanolic sulphuric acid. The chloroform:methanol:reaction mixture was vortexed then agitated for 30 minutes. Following centrifugation, the supernatant was dried under $N_2$. The dried lipids were extracted twice in 400 ul of hydrated n-butanol:HPLC water (1:1) pooled, washed, and dried under $N_2$. To synthesize the methyl esters, 0.75 ml of 2% sulfuric acid in methanol was added to the dried fatty acids, gassed with $N_2$, and incubated for 2 h at 70° C.

Following the addition of 0.75 ml of HPLC grade water, $^{14}$C fatty acid methyl esters were extracted twice with 1.5 ml of pentane, washed with 0.5 ml HPLC water and dried.

$^{14}$C fatty acid methyl esters were separated and identified using reversed phase thin layer chromatography as follows. Reversed-phase thin layer chromatographic plates (20×20 cm, Analtech) were baked in a vacuum oven at 80° C. for 20 minutes. Dried $^{14}$C fatty acid methyl esters and standards were resuspended in 20 ul chloroform:methanol (9:1), spotted, and chromatographed in chloroform: methanol:water (5:15:3). Non-radioactive standards were visualized with cyclodextrin spray in iodine vapor. $^{14}$C fatty acid methyl esters were detected using a Bioscan System 2000 imaging scanner with Autochanger 3000.

Figure 4:
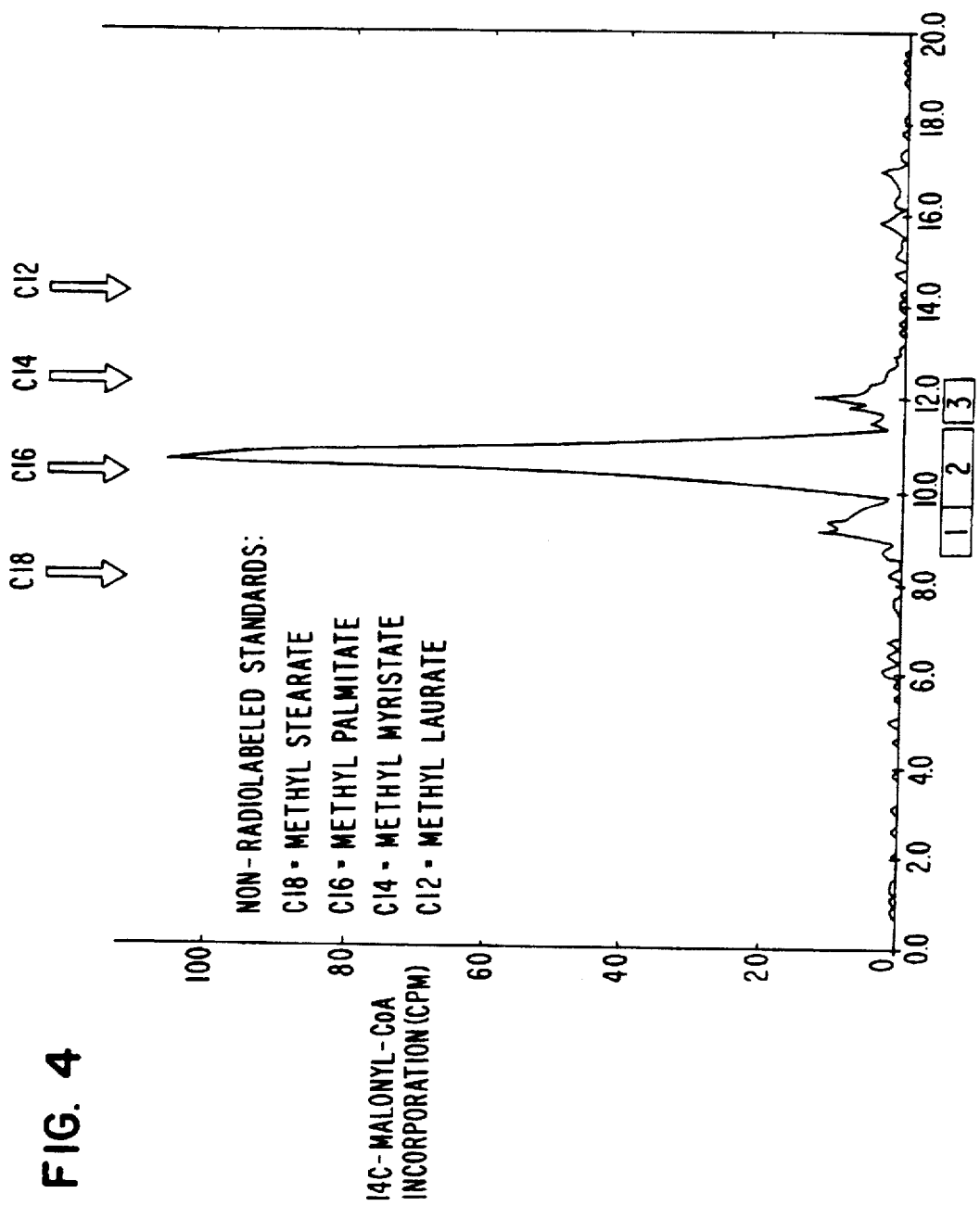
FIG. 4 shows that OA-519 Synthesizes Fatty Acids from Acetyl- and Malonyl-CoA.

Results: OA-519 synthesized 85% palmitate (16 carbon saturated fatty acid), with approximately 6% myristate and 8% stearate (14 and 18 carbon saturated fatty acids, respectively) (FIG. 4). These data demonstrate that OA-519 has fatty acid synthase activity by showing generation of complete fatty acids from $^{14}$C-labeled malonyl-CoA. The ratios among product fatty acids is similar to fatty acid synthase from human liver, but markedly different than that for fatty acid synthase from lactating human breast (34% stearate, 33% palmitate, 16% myristate).

Kinetic Characterization of OA-519 Fatty Acid Synthase

The specific activity of purified OA-519 was determined spectrophotometrically by following the oxidation of NADPH at 340 nm in the presence of acetyl coenzyme A and malonyl coenzyme A. OA-519 has a specific activity of 586 nanomoles NADPH oxidized/min/mg protein which compares favorably with the value of 404 obtained for human liver.

Spectrophotometric studies with OA-519$_{FAS}$ demonstrated that the apparent $K_m$ of 86.2×10$^{-5}$M for malonyl-CoA was higher than the literature values reported for rat or rabbit mammary gland (1.3×10$^{-5}$M or 2.9×10$^{-5}$M, respectively) (Smith, et al., *Methods Enzymol.*, 35:65–74, 1975; Dils, et al., *Methods Enzymol.*, 35:74–83, 1975) or for the synthase from the human breast cancer cell line SKBR3 (1.8×10$^{-5}$M) (Thompson, et al., *Biochim. Biophys. Acta*, 662:125–130, 1981). The $K_m$ for the purified synthase from normal human tissues has not been reported. In contrast to the $K_m$ values, the specific activity of 624 nmol NADPH oxidized/min/mg protein was similar to the reported specific activities of fatty acid synthases purified from a variety of sources including human liver (Roncari, *Methods Enzymol.*, 71:73–39, 1981).

Example 4

Fatty acid synthesis by OA-519 is inhibited by FAS inhibitors.

Cerulenin is a specific inhibitor of the condensing enzyme activity of fatty acid synthase as demonstrated by Funabashi, et al, *J. Biochem.*, 105:751–755, 1989. The drug melarsoprol is a trivalent arsenical compound; trivalent arsenicals react with adjacent thiol groups. Fatty acid synthase activity requires multiple reduced thiol groups which would act as targets for inhibition by melarsoprol.

Using purified OA-519, in the spectrophotometric enzyme assay, cerulenin was shown to be a non-competitive inhibitor of OA-519 fatty acid synthase activity.

Spectrophotometric fatty acid synthase assay: The fatty acid synthase assay was performed in a total volume of 451 ul with the following components:

18.88 ug of purified OA-519 fatty acid synthase from the ZR-75-1 breast carcinoma cell line as described in Example 2, 25 nanomoles acetyl-CoA, 75 nanomoles NADPH, and 50 ul of 1 molar potassium phosphate, pH 6.6 at 25° C. The substrate malonyl-CoA was added at concentrations of 0.5 and 0.6 micromolar in the presence of 0, 9.9, 148, 198, or 397 micromolar cerulenin. HPLC grade water was added to achieve a final volume of 451 ul for all assays.

The enzyme, NADPH, acetyl-CoA, phosphate, cerulenin, and water were combined, vortexed, and incubated in a Beckman DU 650 spectrophotometer at 37° C. Oxidation of NADPH was monitored at 340 nm without substrate to determine background for 2 min. Malonyl-CoA was then added to the reaction cuvette, mixed, and incubated at 37° C. while NADPH oxidation was determined at 10 second intervals at 340 nm in the spectrophotometer for a total of 2 min. All determinations were performed in duplicate.

Figure 5:
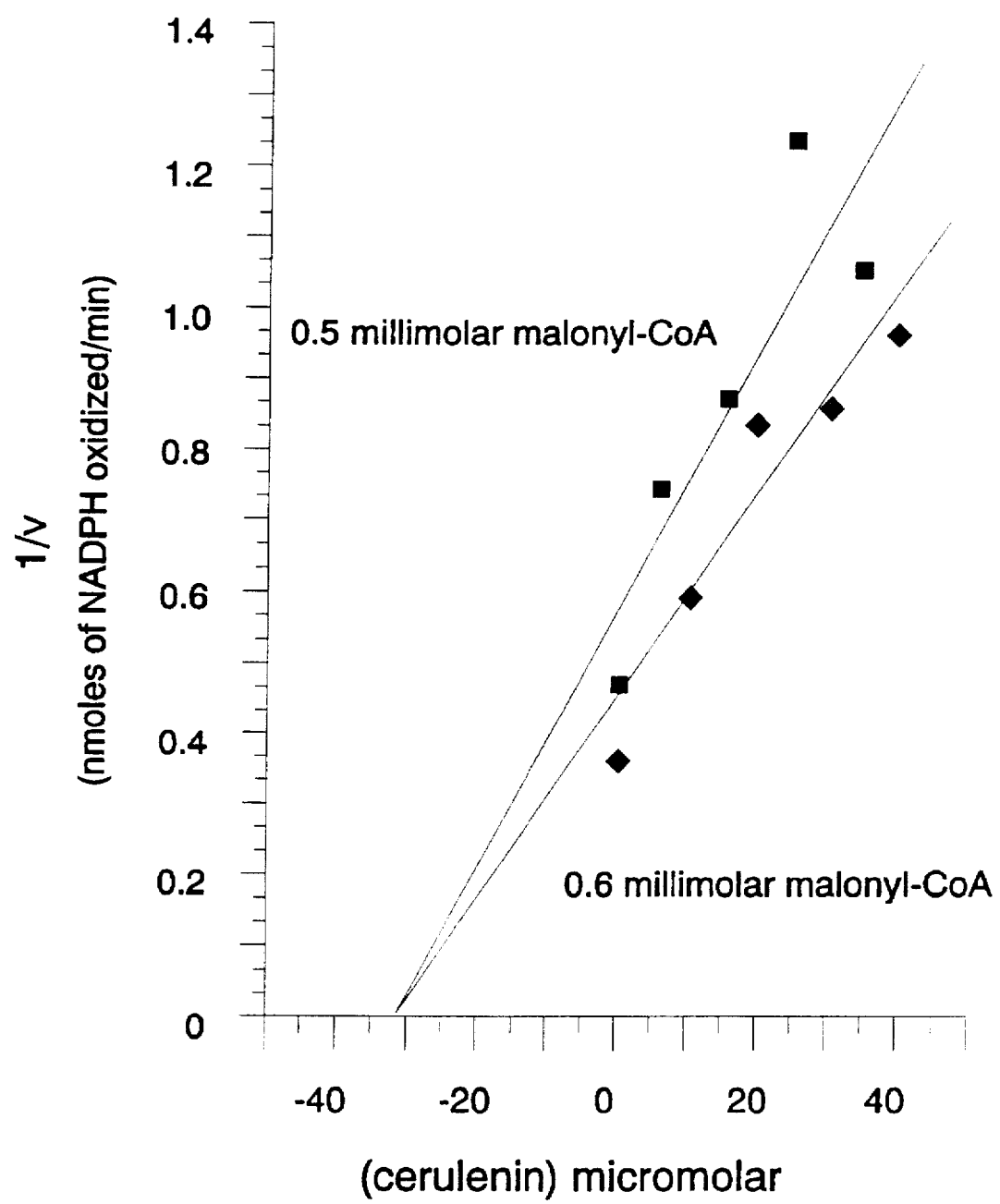
FIG. 5 shows a Dixon Plot of Cerulenin Inhibition of OA-519 Fatty Acid Synthase Activity.

Results. The spectrophotometric data was plotted according to Dixon (Dixon, M., *Biochem. J.*, 55:170–171, 1953) which graphs inhibitor concentration versus 1/v for each given substrate concentration. The analysis in FIG. 5 demonstrates that cerulenin inhibits the OA-519 fatty acid synthase with an apparent $K_i$ of 32 micromolar for the substrate malonyl-CoA. The inhibition also appears to be non-competitive as has been reported for cerulenin (Funabashi, et al, *J. Biochem.*, 105:751–755, 1989), since the curves intersect at the abscissa.

Example 5

Selective Effects of FAS Inhibitors

FAS inhibitors are growth inhibitory to carcinoma cells but not to normal cells. OA-519 is overexpressed in breast carcinomas with poor prognosis but little OA-519 expression is identified in normal tissues. Using standard in vitro growth inhibition assays, two inhibitors of OA-519, cerulenin and melarsoprol, were shown to be anti-proliferative to carcinoma cells but to have little effect on normal human fibroblasts.

In vitro growth inhibition assays for OA-519 inhibition were performed using ZR-75-1 cells or normal human fibroblasts which were grown to confluence, and then 25,000 cells were plated in 1:1 conditioned:fresh medium (RPMI with 10% fetal calf serum) supplemented at a physiologic level to 0.5 millimolar oleic acid bound to previously delipidized bovine serum albumin. Cells were allowed to attach and grow overnight. At time 0, drugs diluted in RPMI medium with 10% fetal calf serum were added to achieve the following concentrations: 50 ug/ml to 0.01 ug/ml with serial two-fold dilutions including no drug and empty well controls. Each concentration was performed in quadruplicate and time points were taken at 4, 8, 24, and 48 h. After drug treatment, cells were stained with crystal violet, solubilized in SDS, and read on a Molecular Diagnostics automated plate reader at 570 nm.

Figure 6:
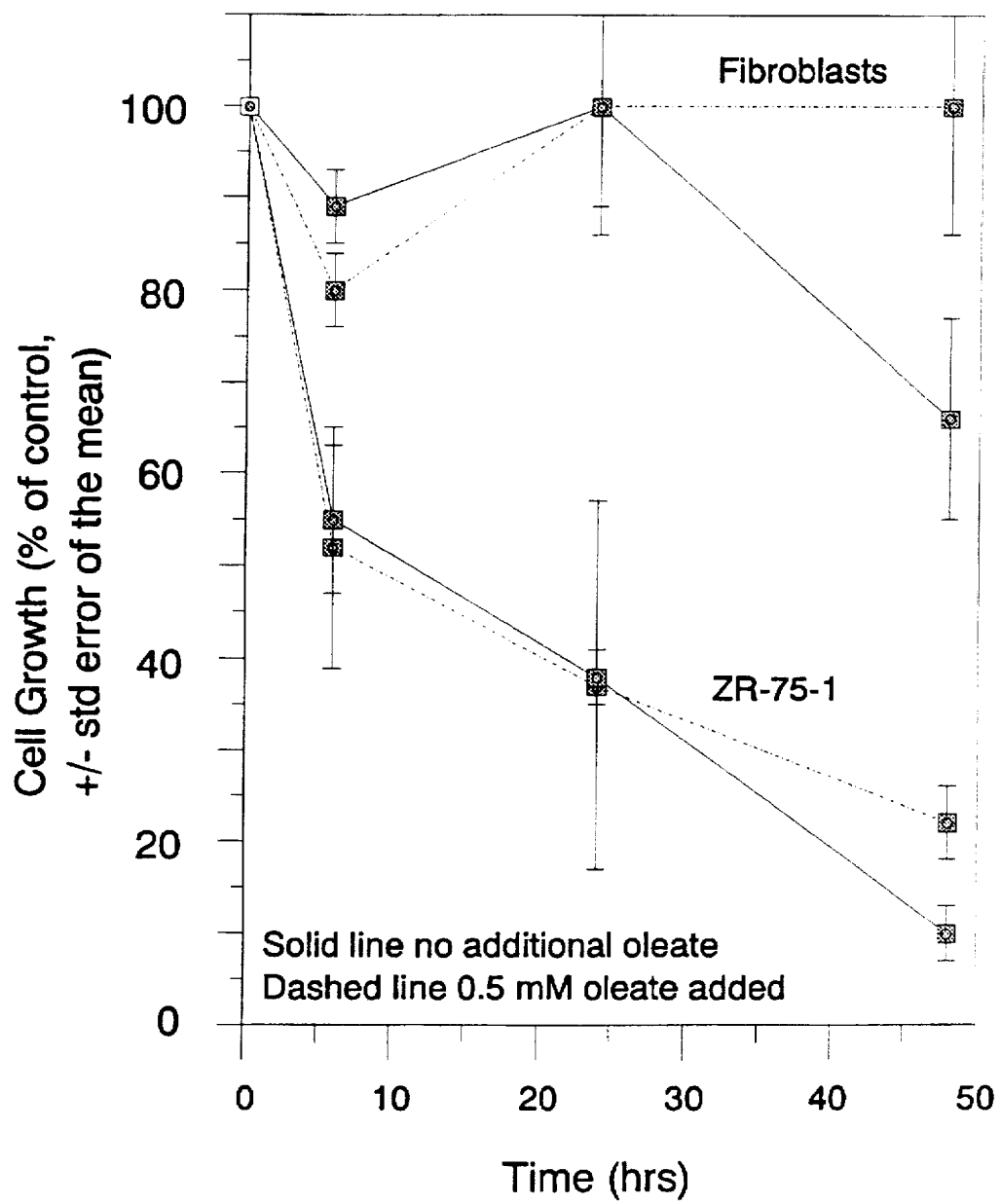
FIG. 6 shows that Cerulenin is Growth Inhibitory to Carcinoma Cells But Not To Normal Cells.

FIG. 6 demonstrates that at a cerulenin concentration of 6.25 ug/ml, normal human fibroblasts are unaffected by the drug, whereas by 48 h, growth of the ZR-75-1 cells was over 80% inhibited. Presence of 0.5 millimolar oleic acid in the culture medium prevented cerulenin growth inhibition in the normal fibroblasts, but not in the breast carcinoma cells. In similar experiments without oleic acid supplementation, growth of both breast carcinoma and normal fibroblasts was inhibited.

Example 6

Cytotoxicity of OA-519 inhibition is related to the level of OA-519 synthase activity Fibroblasts with vanishingly little OA-519 synthase activity are resistant to cerulenin concentrations which inhibit growth by more than 80% of breast carcinoma cells having high levels of OA-519 activity. To show that carcinoma cell lines which express OA-519 are sensitive to OA-519 inhibitors, while those with low OA-519 activity are resistant, multiple breast, prostate, lung, colon, and ovarian carcinoma cell lines, and normal fibroblasts were studied, correlating OA-519 synthase activity and growth inhibition by cerulenin. The relationship between drug sensitivity and OA-519 enzyme activity held for all cell types.

OA-519 fatty acid synthase activity: For each cell type, 200,000 cells were plated in 24 well plates, grown overnight in triplicate. Cells were then scraped, pelleted, and frozen at −80° C. until assayed for OA-519 enzyme activity.

A modified assay was used to measure the OA-519 fatty acid synthase activity, in order to increase the sensitivity by which incorporation of $^{14}$C-malonyl coenzyme A into fatty acid could be measured compared to the spectrophotometric assay used in Example 3. Following a hypotonic lysis of the frozen cell pellets in 1 millimolar DTT, 1 millimolar EDTA, 20 millimolar Tris HCl, pH 7.5 at 25° C., and centrifugation at 14,000× g for 10 minutes, 20 ul of the lysate is added to a reaction mixture containing 75 nanomoles NADPH; 25 nanomoles acetyl coenzyme A; 16.6 ul of 1 molar potassium phosphate, pH 6.6 at 25° C., 97 ul HPLC grade water to a total volume of 150 ul. Following vortexing, 2 ul of $^{14}$C-malonyl coenzyme A (20 uCi/ml; 51 mCi/millimolar) and 25 nanomoles malonyl coenzyme A were added and vortexed. The reaction mixture was incubated at 37° C. for 20 minutes and stopped by the addition of 1 ml of 1:1 chloroform:methanol.

The chloroform:methanol:reaction mixture was vortexed and agitated for 30 minutes. Following centrifugation, the supernatant was dried under $N_2$. The dried lipids were extracted twice in 400 ul of hydrated n-butanol:HPLC water (1:1) pooled, washed, dried under $N_2$, and counted for $^{14}$C.

Growth Inhibition Assay: Anti-proliferative activity of cerulenin for each cell line was determined using the same assay and drug concentrations described in Example 5, except that no oleic acid was added and a single 24 h time point was taken.

Figure 7:
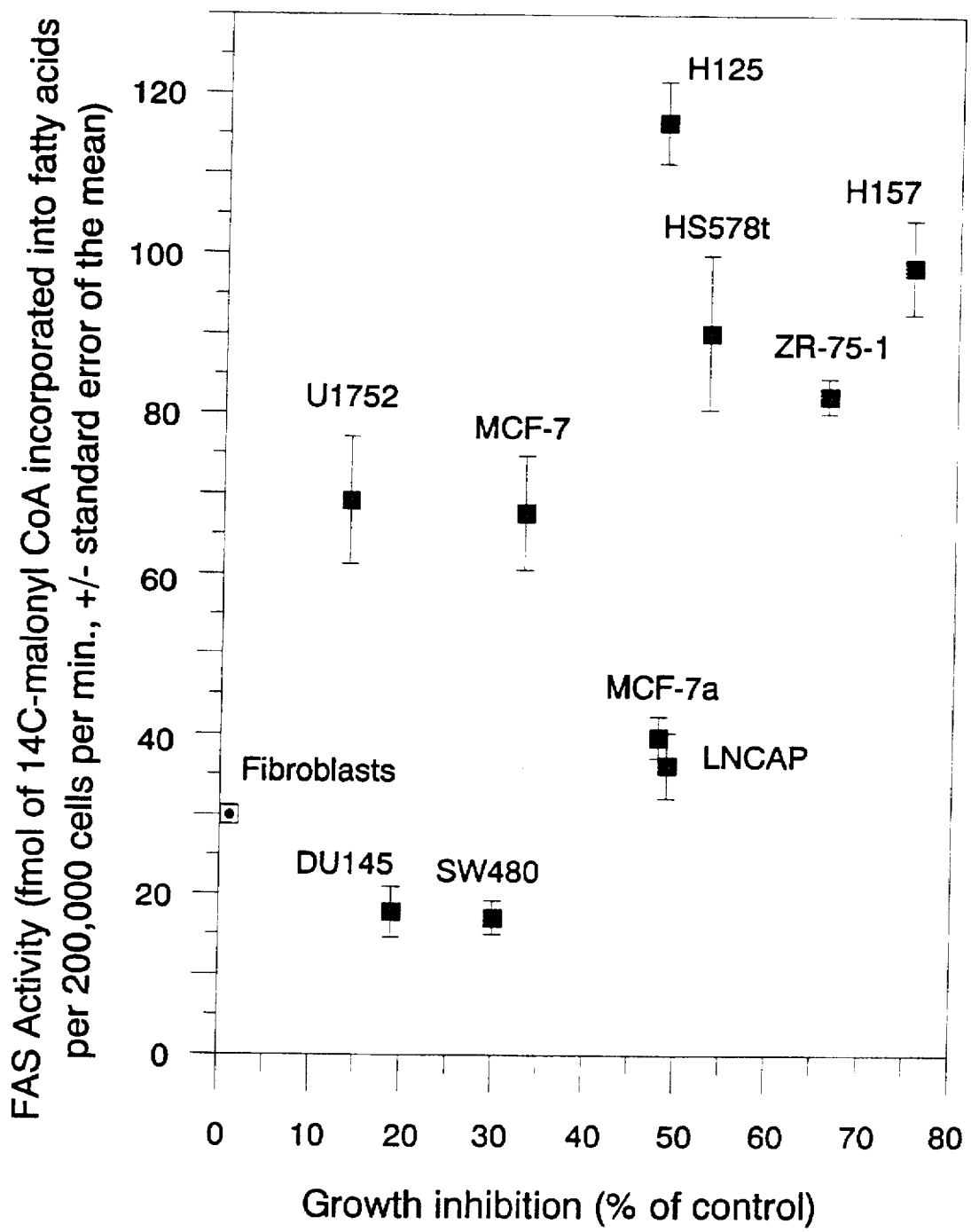
FIG. 7 shows that Cerulenin Inhibition Increases as OA-519 Enzyme Activity Increases.

FIG. 7 shows the relationship between OA-519 enzyme activity and sensitivity of the carcinoma cells to the inhibitor cerulenin. At enzyme activity below 4 picomoles malonyl CoA incorporated into fatty acid per 200,000 cells per minute, less than 50% of the cells were growth inhibited (with the exception of the H125 lung carcinoma line, 11.6 picomoles per minute and 48 % growth inhibition). In contrast, most cell lines with more than 7 picomoles malonyl CoA incorporated into fatty acid per 200,000 cells per minute showed more than 50% growth inhibition. Thus, increasing OA-519 enzyme activity is associated with increased sensitivity to cerulenin anti-proliferative activity. Cells with increased OA-519 enzyme activity appear to be reliant on the OA-519 fatty acid synthase pathway.

Example 7

OA-519 Fatty Acid Synthase Activity Parallels Acyl-glyceride Synthesis in Cancer Cell Lines and Human Fibroblasts Table 3 lists a group of 10 human cell lines with high, intermediate, and low FAS enzyme activity which, along with human embryonic fibroblast lines, have been used in the experiments described herein.

OA-519 synthase activity: For each cell type, 200,000 cells were plated in triplicate in standard 24 well plates, grown overnight, scraped, pelleted, and frozen at −80° C. Following hypotonic lysis of frozen pellets in 1 mM DTT, 1 mM EDTA, 20 mM Tris HCl, pH 7.5 at 25° C., 20 ul of the lysate were added to a reaction mixture followed by addition of $^{14}$C malonyl-CoA. The reaction mixture was incubated at 37° C. for 20 min. and stopped by the addition of 1 ml of 1:1 chloroform:methanol. After a 30 min. extraction, the lipids were dried under $N_2$, twice extracted in 400 ul hydrated n-butanol:water, 1:1, pooled, washed, dried under $N_2$, and counted for $^{14}$C. Activity was normalized to cell number or to total cellular protein. The results are shown in Table 3.

TABLE 3

Characteristics Of Cell Lines Utilized In In-Vitro Experiments

| CELL LINE | ORIGIN | CULTURE MEDIUM | FAS ACTIVITY | |
|---|---|---|---|---|
| SKBR3 | Human Breast ER− | McCoy's + 15% FCS | High[a] | 198.04 |
| ZR-75-1 | Human Breast, ER+ | RPMI + 10% FCS | Intermediate[a] | 38.08 |
| MCF-7 | Human Breast, ER+ | DMEM + 10% FCS | Intermediate[a] | 31.27 |
| MCF-7a | Human Breast, adriamycin Resistant | DMEM + 10% FCS | Low[a] | 18.32 |
| HS-27 | Human Fibroblast | DMEM + 10% FCS | Low[a] | 13.87 |
| SW-480 | Human Colon | Laibovitz + 10% FCS | Low[a] | 7.93 |
| LNCAP | Human Prostate Androgen responsive negative | DMEM + 10% FCS | High[b] | 700 |
| TSU-prl | Human Prostate Androgen responsive negative | DMEM + 10% FCS | High[b] | 700 |
| Dupro 1 | Human Prostate Androgen responsive negative | DMEM + 10% FCS | Intermediate[b] | 400 |
| DU-145 | Human Prostate Androgen responsive negative | DMEM + 10% FCS | Intermediate[b] | 400 |

TABLE 3-continued

Characteristics Of Cell Lines
Utilized In In-Vitro Experiments

| CELL LINE | ORIGIN | CULTURE MEDIUM | FAS ACTIVITY | |
|---|---|---|---|---|
| PC3 | Human Prostate Androgen responsive negative | DMEM + 10% FCS | Low[b] | 140 |

[a]fmol of 14-C-malonyl-CoA incorporated into fatty acids per 200,000 cells per minute.
[b]fmol of 14-C-malonyl-CoA incorporated into fatty acids per µg protein per minute.

Further assays were done to determine whether increased FAS levels were correlated with increased overall fatty acid biosynthesis. Because acetyl CoA carboxylase, the rate-limiting enzyme in the pathway, lies proximal to fatty acid synthase, analysis of acyl-glyceride production from $^{14}$C-acetate may be measured as a reliable indicator of overall pathway activity.

Figure 8:
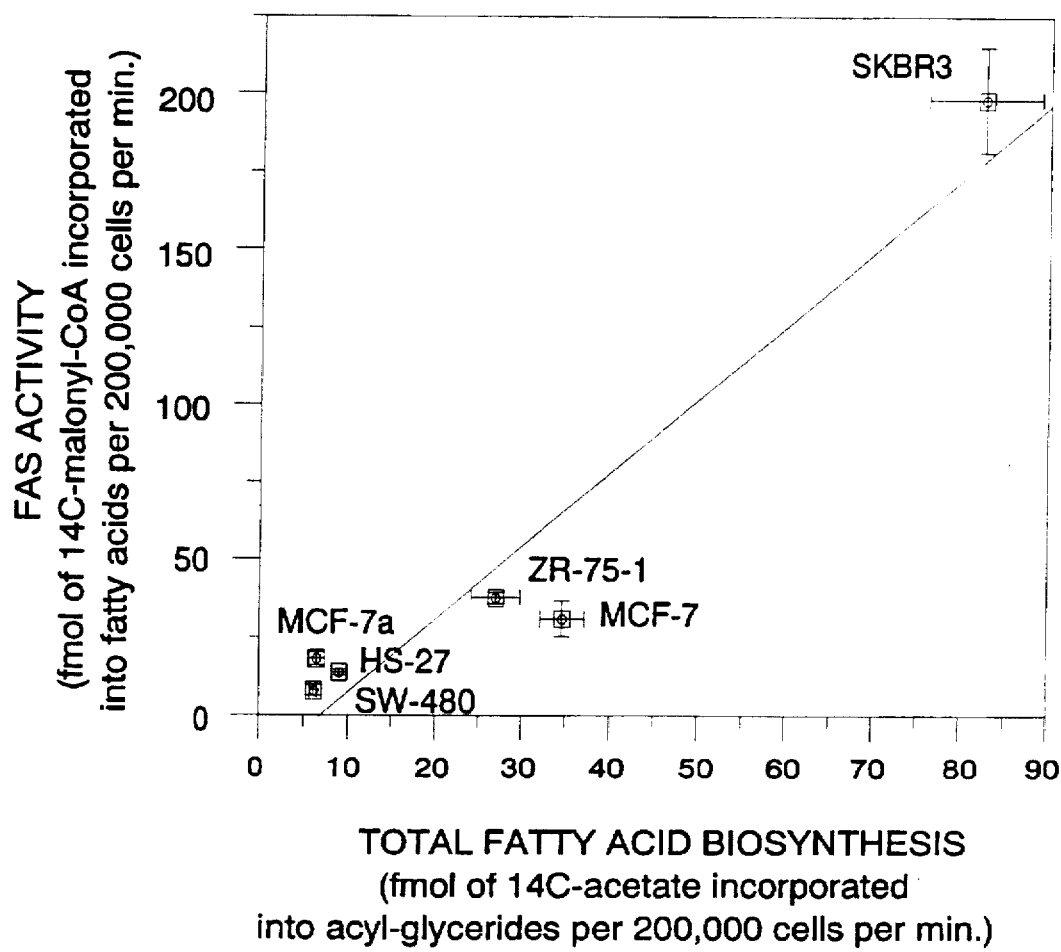
FIG. 8 shows the correlation between FAS expression and acyl-glyceride synthesis.

Measurement of endogenous fatty acid incorporation into acyl-glycerides: For each cell type, 200,000 cells were plated in triplicate for non-polar and polar lipid analysis. Following overnight growth, each well of cells was incubated for 2 hours with 1 uCi $^{14}$C acetate. $^{14}$C-labeled lipids were extracted as above, and dried under $N_2$. For analysis of non-polar lipids, samples were resuspended in 10 ul chloroform and spotted on silica gel N-HR (Brinkmann) and chromatographed in hexane:ethyl ether:acetic acid, 65:25:4 by volume. Cholesterol, palmitic acid, tripalmitin, and cholesterol palmitate (Matreya) were run as controls at 50 ug each. For analysis of polar lipids, samples were spotted on silica get 6A (Whatman) and chromatographed in hexane-:ethyl ether:acetic acid 90:10:1 by volume. 50 ug each of cholesterol, phosphatidyl ethanolamine, lecithin, and lysolecithin (Matreya) were run as controls. $^{14}$C-labeled lipids were detected and quantified using a Bioscan System 2000 imaging scanner with Autochanger 3000. Non-radioactive standards were visualized using rhodamine spray under ultraviolet light. Error bars on FIG. 8 represent the standard error of the mean. Phosphatidylcholine and triglycerides were the predominant acyl-glycerides detected.

As shown in FIG. 8, FAS activity (as measured by $^{14}$C-malonyl-CoA incorporation into total lipids) correlated strongly ($r^2$=0.93) with the overall fatty acid byosynthetic pathway activity (as measured by the rate of $^{14}$C-acetate incorporation into acyl-glycerides). Importantly, TLC analysis demonstrated that during the time course of the experiment, most of the $^{14}$C-acetate was incorporated into phosphatydylcholine with variable quantities of triglycerides or phosphatidylethanolamine. No $^{14}$C-labelled cholesterol esters, free fatty acid, or phosphatidylserine were detected. These data mean that (a) increased FAS activity indicates increased overall fatty acid synthesis, (b) phosphatidylcholine, a major membrane lipid, was the predominant end product of FAS, and (c) the activities of acetyl CoA carboxylase and malic enzyme, which are co-regulated with FAS in normal cells, may also be increased in these cells.

Example 8

Figure 9:
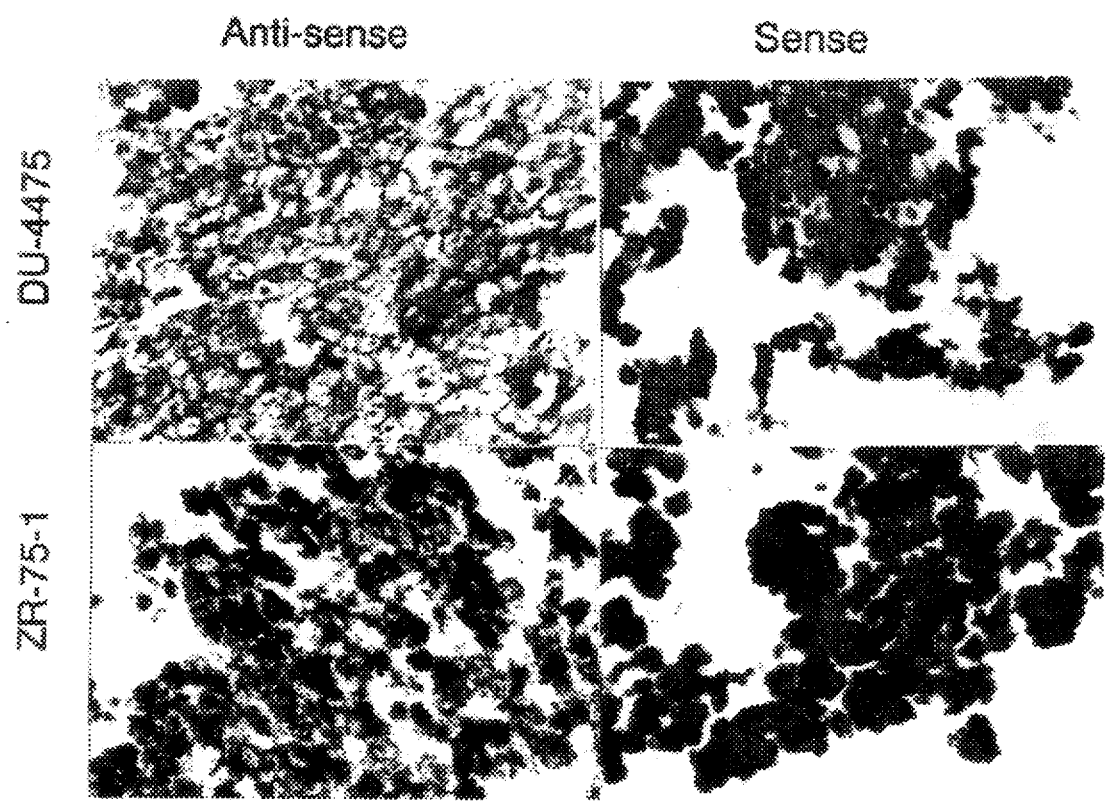
FIG. 9 shows detection of OA-519$_{FAS}$ expression in tumor cell lines by in situ hybridization of riboprobes having FAS sequence.

OA-519 expression analyzed by in situ hybridization cDNA from a ZR-75-1 library yielded a 1.6 kb probe, pFAS 1.6, showing ~85% nucleotide identity with 3'sequences of rat fatty acid synthase cDNA. On Northern blots of total ZR-75-1 RNA, this probe hybridized with a single ~9.5 kb message (data not shown). In situ hybridization for OA-519 in formalin-fixed paraffin-embedded ZR-75-1 and DU-4475 human fibroblast cells using digoxigenin-labeled riboprobes derived from pFAS 1.6 in Bluescript II is shown in FIG. 9. The left panel is anti-sense, while the right panel is the sense control. Anti-sense riboprobes generated from pFAS 1.6 yielded a substantially stronger hybridization signal with ZR-75-1 cells than with DU-4475 cells (FIG. 9), showing that message levels and protein levels were concordant. Thus, cells that express OA-519 can be detected by either immunohistochemistry or in situ hybridization.

These data together suggest that OA-519 over-expression is from increased message levels, due either to increased transcriptional activation or to prolonged message stability. Increased OA-519 levels were not likely due to prolongation of OA-519 protein half-life since OA-519 protein over-expression was accompanied by OA-519 message over-expression. Similarly, experiments finding equivalent pFAS 1.6 hybridization signals among Southern blots of cell lines differing widely in OA-519 expression indicated that over-expression was not likely from gene amplification.

Example 9

Selective Expression of OA-519 in Human Breast Carcinoma

Figure 10:
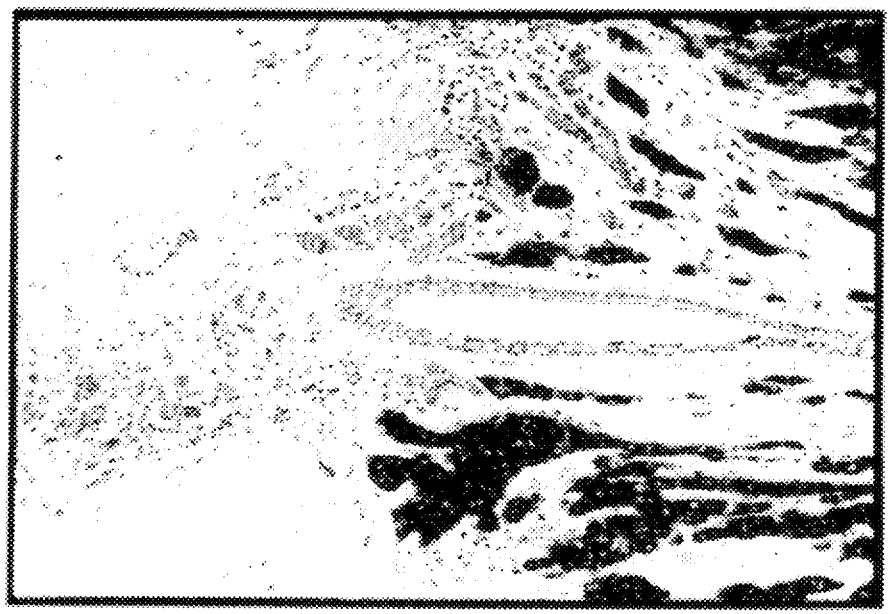
FIG. 10 shows selective expression of OA-519 detected by immunohistochemical staining.

FIG. 10 shows immunohistochemical staining with affinity purified anti-native OA-519 rabbit polyclonal antibodies on a formalin-fixed paraffin-embedded section of infiltrating duct carcinoma. OA-519 was detected using standard biotin-avidin immunohistochemistry with diaminobenzidine as the chromogen. The specificity of expression of FAS is demonstrated in FIG. 10. The cytoplasm of the infiltrating breast cancer cells were strongly reactive with anti-OA-519 antibodies while the adjacent rim of histologically normal breast epithelial and stromal cells was unreactive. Note the intense brown staining in the cytoplasm of the tumors cells indicating OA-519 expression while the normal breast duct and lobule (arrows) and breast stoma were negative. This differential expression of fatty acid synthase between cancer and normal cells forms the basis of the potential selective in vivo inhibition of FAS.

Specific Inhibitors of FAS

The following examples show the effect of cerulenin on tumor cells. Cerulenin, a specific and non-competitive inhibitor of fatty acid synthase, was studied in tumor cells as a representative inhibitor of fatty acid synthesis. Cerulenin covalently binds to a thiol group in the active site of the condensing enzyme of fatty acid synthase, inactivating this key enzymatic step (Funabashi, et al., *J. Biochem.,*

105:751–755, 1989). The condensing enzyme reaction, which catalyzes the condensation of malonyl-CoA with an acetyl group or with the nascent fatty acid chain, generating $CO_2$, is the most specific reaction of the synthase and is not shared by other enzymes. While cerulenin has been noted to possess other activities, these either occur in microorganisms which may not be relevant models of human cells (e.g. inhibition of cholesterol synthesis in fungi, Omura (1976), *Bacteriol. Rev.*, 40:681–697; or diminished RNA synthesis in viruses, Perez, et al. (1991), *FEBS*, 280:129–133), occur at a substantially higher drug concentrations (inhibition of viral HIV protease at 5 mg/ml, Moelling, et al. (1990), *FEBS*, 261:373–377) or may be the direct result of the inhibition of endogenous fatty acid synthesis (inhibition of antigen processing in B lymphocytes and macrophages, Falo, et al. (1987), *J. Immunol.*, 139:3918–3923). Recent data suggests that cerulenin does not specifically inhibit myristoylation of proteins (Simon, et al., *J. Biol. Chem.*, 267:3922–3931, 1992). At the concentrations used in the present studies, cerulenin is a specific growth inhibitor for human tumor cells expressing significant FAS activity, as shown below.

Example 10

Cerulenin Cytotoxicity parallels Acyl-glyceride Synthesis in Cancer Cell Lines and Human Fibroblasts Cerulenin cytotoxicity was studied in two experimental formats. First, clonogenic (limiting dilution) assays tested whether cerulenin was cytotoxic, cytostatic, or had no demonstrable effect. Once cytotoxicity was established, a high-throughput 96 well micro-titer plate assay was used to test various doses on most of the cell lines from Table 3. If cancer cells rely on endogenous fatty acid biosynthesis, it follows that the toxicity of cerulenin should be directly proportional to the level of fatty acid biosynthesis; i.e., cells with higher levels of FAS should be more sensitive to cerulenin.

Clonogenic assay: One million cells were plated in 25 cm sq. flasks. Following overnight incubation, cells were either untreated or treated with cerulenin at 2.5, 5.0 or 10.0 ug/ml for 6 hours. Cells were then trypsinized to a single cell suspension and plated in 16 mm dishes at 1000 or 500 cells per dish in triplicate. Following 3 days incubation for ZR-75-1 and MCF-7 cells, and 7 days for SKBR3 cells, colonies were counted and expressed as the percentage of the untreated control.

As shown in FIG. 11A, treating MCF-7 cells with cerulenin at 10 µg/ml in clonogenic assays resulted in dose-dependent cytotoxicity. Increasing exposure time to 24 hours at 10 µg/ml resulted in greater than three logs of cell kill. Thus cerulenin was cytotoxic to cell lines undergoing endogenous fatty acid synthesis.

Measurement of growth inhibition: Cell lines were plated in 96 well microtiter plates at 5,000 cells per well. Following 18 hours growth, cerulenin (diluted in 10% DMSO) was added to the media to achieve 10 µg/ml. Each time point was performed in quadruplicate with empty well controls. After 24 hour exposure to cerulenin, cells were stained with crystal violet, solubilized in 1% SDS, and were read on a Molecular Diagnostics automated plate reader at 570 nm. Error bars represent standard error of the mean.

Using the microtiter plate cytotoxicity assay, FIG. 11B demonstrates that, after 24 hours exposure to 10 µg/ml cerulenin, relative growth inhibition was directly related to the previously measured rate of fatty acid biosynthesis in all six cell lines. The MCF-7 adriamycin-resistant cell line (MCF-7a) was the only significant exception. Graphing growth inhibition versus FAS activity yielded a similar result (see Example 6, FIG. 7). Thus, growth inhibition to cerulenin was largely predicted by the level of endogenous fatty acid biosynthesis or FAS activity. Importantly, this holds true for both cancer cells and normal embryonic fibroblasts. Therefore, the relationship of cerulenin growth inhibition and fatty acid biosynthesis was not a feature exclusive to transformed cells.

Example 11

Cerulenin Caused Dose-Dependent Inhibition of $^{14}$C-acetate Incorporation into Acyl-glycerides, While Cholesterol Synthesis Was Not Consistently Altered by Cerulenin Measurement of endogenous fatty acid incorporation into acyl-glycerides and cholesterol: For each cell type, 200,000 cells were plated in triplicate for non-polar and polar lipid analysis for each drug, dose in 24 well plates. Following overnight growth, cells were incubated for 6 hours with cerulenin (diluted in 10% DMSO) added to achieve 0, 2.5, 5.0 or 10.0 ug/ml. For the last two hours of cerulenin incubation, 1 uCi of $^{14}$C acetate was added per well. $^{14}$C-labeled lipids were then extracted, chromatographed, and detected as described above. Error bars represent standard error of the mean.

FIG. 12A demonstrates that incorporation of $^{14}$C-acetate into acyl-glycerides was consistently and significantly inhibited in a dose-related manner by cerulenin in six cell lines listed in Table 3. In contrast, FIG. 12B shows that cholesterol synthesis was variably and marginally affected, ranging from mild inhibition in MCF-7 cells to stimulation in SKBR3 cells. These data suggest that cerulenin was not directly affecting enzymes of cholesterol biosynthesis. Furthermore, there was no relationship between the baseline level of cholesterol biosynthesis in these cells and cerulenin growth inhibition (data not shown). Thus cerulenin inhibited acyl-glyceride synthesis in cancer cell lines and fibroblasts with no significant or consistent effect on cholesterol biosynthesis.

Example 12

Cerulenin inhibition is not Correlated with Cell Proliferation

Since OA-$^{519}$FAS expression in clinical breast cancers and some cell lines is independent of proliferation as measured by mitotic index (Kuhajda, et al., *N. Engl. J. Med.*, 321:636–641, 1989), proliferating cell nuclear antigen (PCNA) expression (data not shown) or correlation of FAS expression with cell cycle by flow cytometry (Shurbaji, et al., *Lab. Invest.*, 6869A, 1993), it would be expected that cerulenin anti-proliferative activity would be independent of tumor cell proliferation. Using the microtiter plate assay, doubling times for six cell lines were determined and compared to cerulenin growth inhibition (10 µg/ml, 24 h) There was no correlation between tumor cell doubling times and cerulenin growth inhibition or FAS expression (FIG. 13).

Example 13

Anti-proliferative Activity of Cerulenin Against Prostatic Carcinoma Cells

The antiproliferative activity of cerulenin was also extended to two human androgen-independent prostatic carcinoma lines that exhibited relatively high FAS activities (see Table 3). TSU-pr1 and Dupro-1 cell lines were plated in RPMI-1640 with 10% fetal bovine serum at $3\times10^5$ and $1\times10^5$ cells respectively/T25 flask in a humidified atmosphere of 95% air: 5% $CO_2$. After 24 hours, initial plating density was measured. In addition, media was replaced (control) or cerulenin was added at 2.5–10 µg/ml to duplicate cultures. Forty-eight hours later, cells were trypsinized and viable cells (trypan blue excluding) counted. The number of population doublings was estimated. For both cell lines, a 48-hour exposure to cerulenin (3–4 µg/ml) resulted in 50% inhibition of population doubling, relative to untreated cultures. FIG. 14 shows representative data from one of two independent experiments.

Example 14

Growth Inhibition of Cancer Cell Lines by an Inhibitor of Acetyl CoA Carboxylase TOFA (an inhibitor of acetyl CoA carboxylase) also demonstrated an anti-proliferative effect on a panel of cell lines with varying levels of FAS enzyme activity (shown in Table 3) and fatty acid biosynthesis (shown in FIG. 8). This experiment was performed using the crystal violet growth inhibition assay. Cells with varying degrees of FAS activity were plated at 5000 cells per well in 96 well plates in RPMI-1640 with 10% heat-inactivated fetal bovine serum. After 72 hours of incubation in a humidified 95% air: 5% $CO_2$ atmosphere, varying concentrations (0–500 µg/ml) of TOFA (5-tetradecyloxyl)-2-furoic acid were added and cultures were re-incubated for 48 hours. Plates were then removed and stained with crystal violet as described. Absorbance readings were averaged for each concentration of agent (n=4), control (n=8), and background (n=8). Background readings were subtracted. The concentration of TOFA is plotted against growth (as % of control growth) in FIG. 15.

48-hour exposure to TOFA, an inhibitor of acetyl CoA carboxylase (Halvorson, D. L. and McCune, S. A., Lipids 19: 851–856, 1984) resulted in growth inhibition of the SKBR-3, ZR-75-1, SW480, and $H^S27$ cell lines with ID50s of 4.6, 0.8, 59.8 and 44.7 µg/ml, respectively. TOFA or 5-(tetradecyloxyl)-2-furoic acid, was a more potent inhibitor of the growth of high FAS cell lines (ZR-75-1 and SW80) than of those lines that expressed lower levels of FAS activity (HS27 and SK-8R-3), as shown in FIG. 15.

Example 15

Inhibition of SKBR-3 Cell Growth by Various Inhibitors of Fatty Acid Synthesis In these experiments, cells were plated at 5000 cells per well in a 96-well microtiter plate and maintained in RPMI-1640 with 10% heat-inactivated fetal bovine serum for 72 hours. Next, the compounds indicated in Table 4 were added, and cells were incubated for an additional 48 hours. Growth inhibition was then measured using the crystal violet method.

The concentration of cerulenin required to inhibit the growth of the human SK-BR-3 mammary carcinoma line (shown in Table 3 to be a line with high FAS activity) was similar to that required for growth inhibition of the prostate tumor lines of Example X-4-A. As shown in Table 4, a 48 hour exposure to 3.6 µg/ml resulted in 50% inhibition of growth. Also shown in Table 4, other compounds reported to inhibit enzymes involved in fatty acid biosynthesis potently inhibited the growth of the SK-BR-3 mammary carcinoma line in a similar fashion, with 50% inhibitory doses (ID50) ranging from 0.3–61.4 µg/ml.

Taken together these data show that cerulenin as well as inhibitors of other enzymes of fatty acid synthesis potently inhibit the growth of mammary, colon, and prostatic carcinoma lines. Furthermore, the potency of growth inhibition was proportional to the relative levels of fatty acid biosynthesis exhibited by these cultured cells.

TABLE 4

Growth Inhibition of SK-BR-3 Cell Line by Inhibitors of Enzymes Involved In Endogenous Fatty Acid Biosynthesis

| ENZYME TARGET | COMPOUND | $ID_{50}$ (µg/ml) |
| --- | --- | --- |
| Citrate Lyase | S-carboxymethyl CoA | 61.4 |
| Malic Enzyme | Bromopyruvate | 52.0 |
|  | Gossypol | 3.1 |
|  | N-ethylmaleimide | 0.9 |
| Acetyl CoA Carboxylase | Sethoxydim | 9.5 |
|  | 5-(tetradecyloxyl)-2-furoic acid | 4.6 |
| Fatty Acid Synthase | Cerulenin | 3.6 |
|  | Iodoacetamide | 0.3 |

SK-BR-3 human mammary carcinoma cells, which were shown to have high levels of FAS activity were plated at 5000 cells/well in 96-well microtiter plates and maintained in RPMI-1640 with 10% heat-activated fetal bovine serum in a humidified atmoshphere of 95% air; 5% $CO_2$. After 72 hours, compounds were added and cells were incubated for an additional 48 hours. Plates were stained with crystal violet and absorbances measured as described. The $ID_{50}$ represents the dose of compound which resulted in 50% reduction of control absorbance, as measured and analyzed in quadruplicate.

Example 16

Synergy Between Triacsin-C and Cerulenin 96 well microtiter plates were plated with ZR-75-1 cells at 25,000 cells/well and incubated overnight (18 h) at 37° C. in 5% $CO_2$. Triacsin-C was added to achieve the following micromolar concentrations in the presence of 0, 2.5, 5.0 or 10.0 ug/ml cerulenin: 50, 25, 12.5, 6.2, 3.1, 1.6, 0.8, 0.4, 0.2, 0.1 and 0. Each concentration was performed in quadruplicate. Cells were incubated for 24 hours, washed in PBS, solubilized in 1% SDS, stained with 0.2% crystal violet in 2% ethanol, and read at 490 nm on a Molecular Diagnostics plate reader.

FIG. 16 shows that triacsin-C is growth inhibitory to cells of a tumor cell line (ZR-75-1) that expresses OA-519$_{FAS}$. When cerulenin was added at a level approximating its $ID_{50}$, the $ID_{50}$ for triacsin-C was lowered from about 15 µM to less than 1 µM, demonstrating the synergistic effect exhibited by the combination of these two inhibitors.

Example 17

High Concentrations of Exogenous Oleate Rescues ZR-75-1 Cells from Growth Inhibition by Cerulenin FIG. 17 demonstrates that cerulenin inhibition of in ZR-75-1 cell growth is reversible with high concentrations of exogenous oleate. ZR-75-1 cells (5,000 per well) were plated in 96 well microtiter plates in medium supplemented with 0, 0.5, 1.0 or 1.5 mM oleate bound to delipidized bovine serum albumin at a molar ration of 4:1. After 18 hours incubation, cerulenin was added at a dose of 10 ug/ml. Cells were stained and assayed as in Example 10 after 24 hours (FIG. 17, upper line) or 48 hours (lower line). The middle line of FIG. 17 represents cells which were re-fed at 24 hours with medium containing the respective oleate concentration without cerulenin and assayed after a 48 hour total incubation. Error bars represent standard error of the mean.

In the top curve of FIG. 17, where cells were exposed to 10 μg/ml cerulenin for 24 hours in the presence of 0, 0.5, 1.0 or 1.5 mM oleate, the 1.5 mM concentration of oleate achieved virtually complete reversal of growth inhibition by cerulenin. When the cells are allowed to incubate for 48 hours, significant toxicity occurred as demonstrated by the lower curve, which was not reversed by oleate. If the anti-proliferative activity seen at 48 hours were due to depletion of oleate in the medium, re-feeding the cells at 24 hours with fresh medium containing the same respective oleate concentration, but without additional cerulenin, should rescue the cells. The middle curve shows the effect of re-feeding the cells at 24 hours, which indeed rescued the cells after 48 hours with 1.5 mM oleate. When oleate was absent, the refed and nonrefed cells showed similar cerulenin-mediated growth inhibition.

This experiment demonstrates that rescue from the anti-proliferative activity of cerulenin was due to the additional fatty acid, and not to glucose or other substances such as growth factors present in the medium. Interestingly, cell lines with low FAS activity such as SW-480 and normal human fibroblasts, required a lower (0.5 mM), physiologic concentration of oleate to achieve rescue from cerulenin growth inhibition (see Example 5). The level of oleate required to rescue ZR-75-1 cells (1.5 mM) is superphysiological, and it is unlikely that this level could be achieved by a diet containing elevated fatty acid content. Taken together these data suggest that cerulenin acts by creating a state of fatty acid starvation leading to cell death, which is proportional to the level of endogenous fatty acid synthesis.

It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertains, and these aspects and modifications are within the scope of the invention, which is limited only by the appended claims.

We claim:

1. A method of inhibiting growth of tumor cells in an animal, said cells expressing at least one enzyme of the fatty acid biosynthetic pathway, comprising administering an inhibitor of fatty acid synthesis to the tumor cells in an amount specifically cytotoxic to said tumor cells, wherein the inhibitor of fatty acid synthesis inhibits lipid biosynthesis by a cell as demonstrated by inhibition of growth in vitro of a tumor cell expressing fatty acid synthase (FAS), said inhibition of growth in vitro being reversed by oleate.

2. A method of inhibiting growth of tumor cells in an animal, said tumor cells expressing a protein exhibiting fatty acid synthase (FAS) activity, comprising administering an inhibitor of fatty acid synthesis to said animal in an amount specifically cytotoxic to said tumor cells, wherein the inhibitor of fatty acid synthesis inhibits lipid biosynthesis by a cell as demonstrated by inhibition of growth in vitro of a tumor cell expressing FAS, said inhibition of growth in vitro being reversed by oleate.

3. A method of inhibiting growth of tumor cells in an animal according to either of claims 1 or 2, comprising administering to the animal a pharmaceutical composition comprising an inhibitor of fatty acid synthesis, wherein the administration of non-invasive.

4. A method according to claim 3, wherein said inhibitor of fatty acid synthesis is formulated in a pharmaceutical composition suitable for topical application.

5. A method according to any of claims 1 or 2, wherein said inhibitor of fatty acid synthesis is formulated in liposomes.

6. The method according to any of claims 1 or 2, wherein the inhibitor is cerulenin.

7. The method according to any of claims 1 or 2, wherein the inhibitor is cerulenin.

8. The method according to any of claims 1 or 2, wherein said animal has a carcinoma selected from the group consisting of breast carcinoma, rectal carcinoma, prostate carcinoma, ovarian carcinoma and colon carcinoma.

9. A method according to any of claims 1 or 2, further comprising the step of down-regulating fatty acid synthase expression of normal tissue.

10. A method according to claim 9, wherein the step of down-regulating fatty acid synthase expression comprises reducing the caloric intake of said animal.

11. A method according to claim 9, wherein the step of down-regulating fatty acid synthase expression comprises administering a composition containing long chain free fatty acid or acyl glyceride to said animal.

12. A method according to claim 11, wherein the composition containing long chain free fatty acid or acyl glyceride supplies essential fatty acids to said animal.

13. The method according to any of claims 1 or 2, further wherein the inhibitor of fatty acid synthesis is an inhibitor of an enzyme selected from the group consisting of fatty acid synthase, acetyl CoA carboxylase, citrate lyase, and malic enzyme.

14. The method according to claim 13, wherein the enzyme is fatty acid synthase (FAS).

15. The method according to claim 13, wherein the enzyme is acetyl CoA carboxylase.

16. The method according to claim 15, wherein the inhibitor is 5-(tetradecyloxy)-2-furoic acid (TOFA).

17. The method according to any one of claims 1 or 2, further wherein an inhibitor of lipid biosynthesis is co-administered with the inhibitor of fatty acid synthesis.

18. The method according to claim 17, wherein the inhibitor of lipid biosynthesis is Triacsin C.

19. The method according to any of claims 1 or 2, wherein said animal has a carcinoma of germ cell origin, a mesothelioma, or a carcinoma selected from the group consisting of carcinoma of the bladder, salivary gland, skin adnexa, bile duct, endocervix, ectocervix, vagina, esophagus, nasopharynx, and oropharynx.

20. The method according to any of claims 1 or 2, wherein said animal has a melanoma or a carcinoma or adenocarcinoma of the stomach, endometrium, kidney, liver or lung.

21. The method according to any of claims 1 or 2, wherein said animal has a dysplastic or neoplastic lesion selected from the group consisting of cutaneous epithelial dysplasia, basal cell carcinoma, squamous cell carcinoma, neoplasm of a skin adnexal structure, a melanocytic dysplasia or neoplasm, a neoplasm secondarily involving skin, a Merkel cell tumor; and a dysplasia or neoplasm of the urinary bladder.

22. The method of claim 12, wherein
said squamous cell carcinoma is selected from the group consisting of actinic keratosis, actinic cheilitis, cornu cutaneum, keratoacanthoma, squamous cell carcinoma in situ, and invasive squamous cell carcinoma; or said neoplasm of skin adnexal structure is selected from the group consisting of apocrine carcinoma, sebaceous carcinoma, and eccrine carcinoma; or said melanocytic dysplasia or neoplasm is cutaneous melanoma; or said neoplasm secondarily involving skin is selected from the group consisting of Paget's disease and extramammary Paget's disease; or said dysplasia or neoplasm of the urinary bladder is transitional cell carcinoma.

23. A method of inhibiting growth of tumor cells in an animal, said cells expressing at least on enzyme of the fatty acid biosynthetic pathway, comprising detecting tumor cells expressing at least one enzyme of fatty acid biosynthetic pathway in said animal, and administering an inhibitor of fatty acid synthesis to said animal in an amount specifically cyotoxic to said tumor cells.

wherein the inhibitor of fatty acid synthesis inhibits growth in vitro of a tumor cell expressing fatty acid synthase (FAS), said inhibition of growth in vitro being reversed by oleate.

24. The method of inhibiting growth of tumor cells in an animal according to claim 23, wherein the at least one enzyme of the fatty acid biosynthetic pathway is FAS.

25. A method of inhibiting growth of tumor cells in an animal according to either of claims 23 or 24, comprising administering to the animal a pharmaceutical composition comprising an inhibitor of fatty acid synthesis, wherein the administration is substantially non-systemic.

26. A method according to claim 25, wherein said inhibitor of fatty acid synthesis is formulated in a pharmaceutical composition suitable for topical application.

27. A method according to any of claims 23 or 24, wherein said inhibitor of fatty acid synthesis is formulated in liposomes.

28. The method according to any of claims 23 or 24, wherein the inhibitor is cerulenin.

29. The method according to any one of claims 25 or 26, wherein the inhibitor is cerulenin.

30. A method according to any of claims 23 or 24, wherein said animal has a carcinoma selected from the group consisting of breast carcinoma, rectal carcinoma, prostate carcinoma, ovarian carcinoma and colon carcinoma.

31. A method according to any of claims 23 or 24, further comprising the step of down-regulating fatty acid synthase expression of normal tissue.

32. A method according to claim 31, wherein the step of down-regulating fatty acid synthase expression comprises reducing the caloric intake of said animal.

33. A method according to claim 31, wherein the step of down-regulating fatty acid synthase expression comprises administering a composition containing long chain free fatty acid or acyl glyceride to said animal.

34. A method according to claim 33, wherein the composition containing long chain free fatty acid or acyl glyceride supplies essential fatty acids to said animal.

35. The method according to any of claims 23 or 24, further wherein the inhibitor of fatty acid synthesis is an inhibitor of an enzyme selected from the group consisting of fatty acid synthase, acetyl CoA carboxylase, citrate lyase, and malic enzyme.

36. The method according to claim 35, wherein the enzyme is fatty acid synthase (FAS).

37. The method according to claim 35, wherein the enzyme is acetyl CoA carboxylase.

38. The method according to claim 37, wherein the inhibitor is 5-(tetradecyloxy)-2-furoic acid (TOFA).

39. The method according to any one of claims 23 or 24, further wherein an inhibitor of lipid biosynthesis is co-administered with the inhibitor of fatty acid synthesis.

40. The method according to claim 39, wherein the inhibitor of lipid biosynthesis is Triacsin C.

* * * * *